(12) United States Patent
Fang et al.

(10) Patent No.: US 8,697,733 B2
(45) Date of Patent: Apr. 15, 2014

(54) PYRIDINE DERIVATIVES AS SPHINGOSINE 1-PHOSPHATE (S1P) RECEPTOR MODULATORS

(71) Applicant: Allergan, Inc., Irvine, CA (US)

(72) Inventors: Wenkui K. Fang, Irvine, CA (US); Liming Wang, Irvine, CA (US); Evelyn G. Corpuz, Irvine, CA (US); Ken Chow, Newport Coast, CA (US); Wha-Bin Im, Irvine, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 13/923,196

(22) Filed: Jun. 20, 2013

(65) Prior Publication Data

US 2013/0338195 A1 Dec. 19, 2013

Related U.S. Application Data

(62) Division of application No. 13/760,781, filed on Feb. 6, 2013, now Pat. No. 8,492,410, which is a division of application No. 13/294,604, filed on Nov. 11, 2011, now Pat. No. 8,399,492.

(60) Provisional application No. 61/419,276, filed on Dec. 3, 2010.

(51) Int. Cl.
*A61K 31/4439* (2006.01)
*A61P 17/06* (2006.01)
*A61P 37/06* (2006.01)

(52) U.S. Cl.
USPC .......... 514/340; 514/336; 514/277; 514/364; 514/352; 514/332; 514/333; 546/269.4; 546/304; 546/280.4; 546/281.4; 548/131

(58) Field of Classification Search
USPC .......... 514/340, 336, 277, 352, 364, 332, 333; 546/269.4, 304, 280.4, 281.4; 548/131
See application file for complete search history.

(56) References Cited

FOREIGN PATENT DOCUMENTS

| WO | 2004-103279 | 12/2004 |
|---|---|---|
| WO | 2008-076356 | 6/2008 |
| WO | 2008-091967 | 7/2008 |
| WO | 2011-0084875 | 1/2011 |

OTHER PUBLICATIONS

Cross, L.C. et al., Rules for the Nomencalture of Organic Chemistry Section E: Stereochemistry, Pure Appli. Chem. (1976), 45, 11-30.
Stahl, Heinrich et al., Handbook of Pharmaceutical Salts, Verlag Helvetica Chimica Acta—Zurich, 2002, 329-345.
Vaccaro, Wayne et al., "Inhibitors of Acyl CoA:Cholesterol Acyltransferase", Journal of Medicinal Chemistry, 1996, 39(8), 1704-1719.
Schurer, S.C., "Ligand-Binding Pocker Shape Differences Between Sphingosine 1-Phosphate (S1P) Receptors S1P1 and S1P3 Determine Efficiency of Chemical Probe Identification by Ultrahigh-Throughput Screening," ACS Chemical Biology, vol. 3, No. 8, Aug. 15, 2008, pp. 486-498.
International Search Report for PCT/US2011/060342, Feb. 8, 2012.

*Primary Examiner* — Sreeni Padmanabhan
*Assistant Examiner* — Irina Neagu
(74) *Attorney, Agent, or Firm* — Doina G. Ene

(57) ABSTRACT

The present invention relates to novel pyridine derivatives, processes for preparing them, pharmaceutical compositions containing them and their use as pharmaceuticals as modulators of sphingosine-1-phosphate receptors.

8 Claims, No Drawings

PYRIDINE DERIVATIVES AS SPHINGOSINE 1-PHOSPHATE (S1P) RECEPTOR MODULATORS

CROSS REFERENCE TO RELATED APPLICATIONS

This application is a divisional application of U.S. Divisional patent application Ser. No. 13/760,781, filed Feb. 6, 2013, which is a divisional application of U.S. Non-Provisional patent application Ser. No. 13/294,604, filed Nov. 11, 2011, which claims the benefit of U.S. Provisional Patent Application Ser. No. 61/419,276 filed Dec. 3, 2010, all of which are incorporated herein by reference in their entirety.

FIELD OF THE INVENTION

The present invention relates to novel pyridine derivatives, processes for preparing them, pharmaceutical compositions containing them and their use as pharmaceuticals, as modulators of sphingosine-1-phosphate receptors. The invention relates specifically to the use of these compounds and their pharmaceutical compositions to treat disorders associated with sphingosine-1-phosphate (S1P) receptor modulation.

BACKGROUND OF THE INVENTION

Sphingosine-1 phosphate is stored in relatively high concentrations in human platelets, which lack the enzymes responsible for its catabolism, and it is released into the blood stream upon activation of physiological stimuli, such as growth factors, cytokines, and receptor agonists and antigens. It may also have a critical role in platelet aggregation and thrombosis and could aggravate cardiovascular diseases. On the other hand the relatively high concentration of the metabolite in high-density lipoproteins (HDL) may have beneficial implications for atherogenesis. For example, there are recent suggestions that sphingosine-1-phosphate, together with other lysolipids such as sphingosylphosphorylcholine and lysosulfatide, are responsible for the beneficial clinical effects of HDL by stimulating the production of the potent antiatherogenic signaling molecule nitric oxide by the vascular endothelium. In addition, like lysophosphatidic acid, it is a marker for certain types of cancer, and there is evidence that its role in cell division or proliferation may have an influence on the development of cancers. These are currently topics that are attracting great interest amongst medical researchers, and the potential for therapeutic intervention in sphingosine-1-phosphate metabolism is under active investigation.

SUMMARY OF THE INVENTION

A group of novel pyridine derivatives which are potent and selective sphingosine-1-phosphate modulators has been discovered. As such, the compounds described herein are useful in treating a wide variety of disorders associated with modulation of sphingosine-1-phosphate receptors. The term "modulator" as used herein, includes but is not limited to: receptor agonist, antagonist, inverse agonist, inverse antagonist, partial agonist, partial antagonist.

This invention describes compounds of Formula I, which have sphingosine-1-phosphate receptor biological activity. The compounds in accordance with the present invention are thus of use in medicine, for example in the treatment of humans with diseases and conditions that are alleviated by S1P modulation.

In one aspect, the invention provides a compound having Formula I or a pharmaceutically acceptable salt thereof or stereoisomeric forms thereof, or the geometrical isomers, enantiomers, diastereoisomers, tautomers, zwitterions and pharmaceutically acceptable salts thereof:

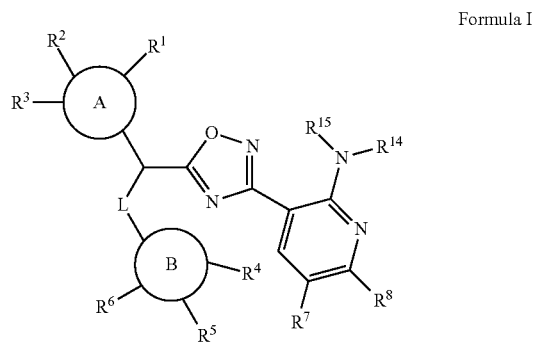

Formula I wherein:
A is $C_{6-10}$ aryl, heterocycle, $C_{3-8}$ cycloalkyl or $C_{3-8}$ cycloalkenyl;
B is $C_{6-10}$ aryl, heterocycle, $C_{3-8}$ cycloalkyl or $C_{3-8}$ cycloalkenyl;
$R^1$ is H, halogen, —$OC_{1-8}$ alkyl, $C_{1-8}$ alkyl, CN, $C(O)R^{11}$, $NO_2$, $NR^{12}R^{13}$ or hydroxyl;
$R^2$ is H, halogen, —$OC_{1-8}$ alkyl, $C_{1-8}$ alkyl, CN, $C(O)R^{11}$, $NO_2$, $NR^{12}R^{13}$ or hydroxyl;
$R^3$ is H, halogen, —$OC_{1-8}$ alkyl, $C_{1-8}$ alkyl, CN, $C(O)R^{11}$, $NO_2$, $NR^{12}R^{13}$ or hydroxyl;
$R^4$ is H, halogen, —$OC_{1-6}$ alkyl, $C_{1-8}$ alkyl, CN, $C(O)R^{11}$, $NR^{12}R^{13}$ or hydroxyl;
$R^5$ is H, halogen, —$OC_{1-8}$ alkyl, $C_{1-8}$ alkyl, CN, $C(O)R^{11}$, $NR^{12}R^{13}$ or hydroxyl;
$R^6$ is H, halogen, —$OC_{1-8}$ alkyl, $C_{1-8}$ alkyl, CN, $C(O)R^{11}$, $NR^{12}R^{13}$ or hydroxyl;
$R^7$ is H, halogen, —$OC_{1-8}$ alkyl, $C_{1-8}$ alkyl, CN, $C(O)R^{11}$, $NR^{12}R^{13}$ or hydroxyl;
$R^8$ is H, halogen, —$OC_{1-8}$ alkyl, $C_{1-8}$ alkyl, CN, $C(O)R^{11}$, $NR^{12}R^{13}$ or hydroxyl;
L is O, S, NH or $CH_2$;
$R^{11}$ is H or $C_{1-6}$ alkyl;
$R^{12}$ is H or $C_{1-6}$ alkyl;
$R^{13}$ is H or $C_{1-6}$ alkyl;
$R^{14}$ is H, $C_{1-6}$ alkyl or $C_{3-6}$ cycloalkyl; and
$R^{15}$ is H, $C_{1-6}$ alkyl or $C_{3-6}$ cycloalkyl.

In another aspect, the invention provides a compound having Formula I wherein L is $CH_2$.

In another embodiment, the invention provides a compound having Formula I wherein:
A is $C_6$ aryl or heterocycle;
B is $C_6$ aryl or $C_{3-8}$ cycloalkyl;
$R^1$ is H, halogen, —$OC_{1-6}$ alkyl, $C_{1-6}$ alkyl or $NO_2$;
$R^2$ is H, halogen, —$OC_{1-6}$ alkyl, $C_{1-6}$ alkyl or $NO_2$;
$R^3$ is H, halogen, —$OC_{1-6}$ alkyl, $C_{1-6}$ alkyl or $NO_2$;
$R^4$ is H, halogen or $C_{1-6}$ alkyl,
$R^5$ is H, halogen or $C_{1-6}$ alkyl;
$R^6$ is H, halogen or $C_{1-6}$ alkyl;
$R^7$ is H, halogen or $C_{1-6}$ alkyl;
$R^8$ is H, halogen or —$C_{1-6}$ alkyl; and
L is $CH_2$.

In another embodiment, the invention provides a compound having Formula I wherein:

A is phenyl, thiophene or pyridine;

B is phenyl, cyclohexyl or cyclopentyl;

$R^1$ is H, chloro, bromo, fluoro, trifluoromethyl, methyl, ethyl, methoxy or —$NO_2$;

$R^2$ is H, chloro, bromo, fluoro, trifluoromethyl, methyl, ethyl, methoxy or —$NO_2$, $R^3$ is H, chloro, bromo, fluoro, trifluoromethyl, methyl, ethyl, methoxy or —$NO_2$;

$R^4$ is H, methyl, chloro or iso-butyl;

$R^5$ is H, methyl, chloro or iso-butyl;

$R^6$ is H, methyl, chloro or iso-butyl;

$R^7$ is H;

$R^8$ is H; and

L is $CH_2$.

In another embodiment, the invention provides a compound having Formula I wherein:

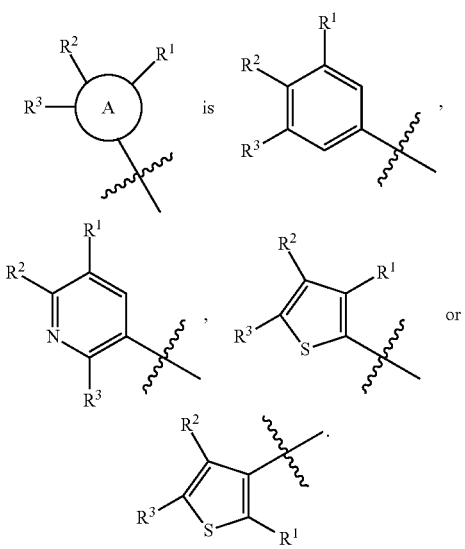

In another embodiment, the invention provides a compound having Formula I wherein:

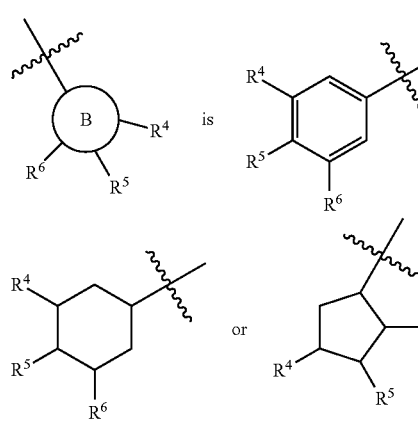

In another embodiment, the invention provides a compound having Formula I wherein:

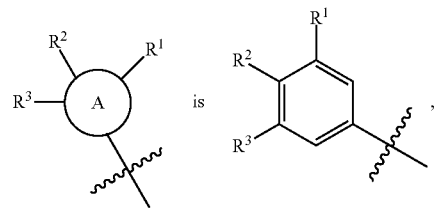

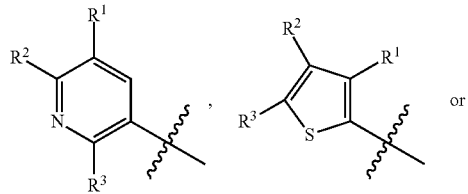

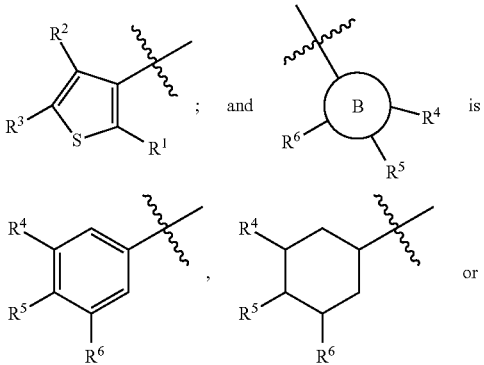

In another embodiment, the invention provides a compound having Formula I wherein:

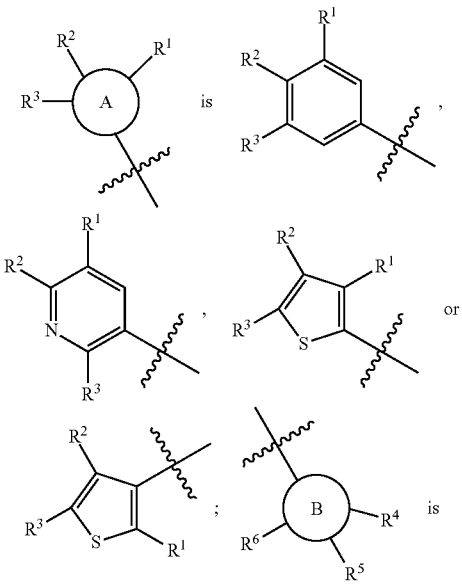

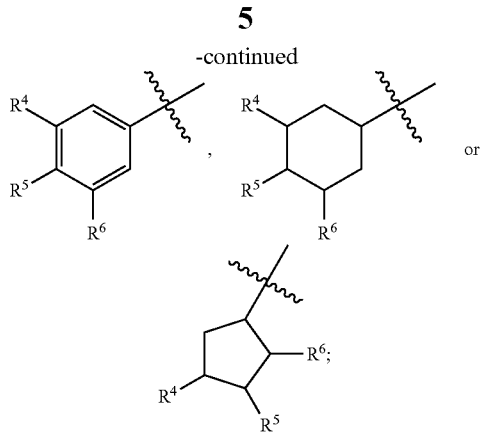

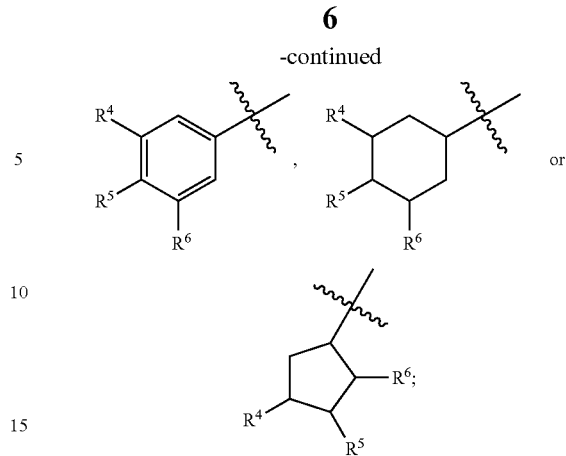

R[1] is H, halogen, —OC$_{1-6}$ alkyl, C$_{1-6}$ alkyl, CN, C(O)R[11], NO$_2$, NR[12]R[13] or hydroxyl;
R[2] is H, halogen, —OC$_{1-6}$ alkyl, C$_{1-6}$ alkyl, CN, C(O)R[11], NO$_2$, NR[12]R[13] or hydroxyl;
R[3] is H, halogen, —OC$_{1-6}$ alkyl, C$_{1-6}$ alkyl, CN, C(O)R[11], NO$_2$, NR[12]R[13] or hydroxyl;
R[4] is H, halogen, —OC$_{1-6}$ alkyl, C$_{1-6}$ alkyl, CN, C(O)R[11], NR[12]R[13] or hydroxyl;
R[5] is H, halogen, —OC$_{1-6}$ alkyl, C$_{1-6}$ alkyl, CN, C(O)R[11], NR[12]R[13] or hydroxyl;
R[6] is H, halogen, —OC$_{1-6}$ alkyl, C$_{1-6}$ alkyl, CN, C(O)R[11], NR[12]R[13] or hydroxyl;
R[7] is H, halogen, —OC$_{1-6}$ alkyl, C$_{1-6}$ alkyl, CN, C(O)R[11], NR[12]R[13] or hydroxyl;
R[8] is H, halogen, —OC$_{1-6}$ alkyl, C$_{1-6}$ alkyl, CN, C(O)R[11], NR[12]R[13] or hydroxyl;
L is CH$_2$;
R[11] is H or C$_{1-6}$ alkyl;
R[12] is H or C$_{1-6}$ alkyl;
R[13] is H or C$_{1-6}$ alkyl.
R[14] is H, C$_{1-6}$ alkyl or C$_{3-6}$ cycloalkyl; and
R[15] is H, C$_{1-6}$ alkyl or C$_{3-6}$ cycloalkyl.

In another embodiment, the invention provides a compound having Formula I wherein:

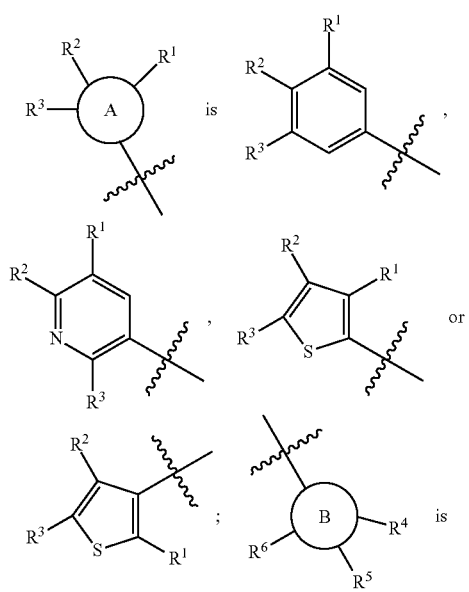

R[1] is H, halogen, —OC$_{1-6}$ alkyl, C$_{1-6}$ alkyl or NO$_2$;
R[2] is H, halogen, —OC$_{1-6}$ alkyl, C$_{1-6}$ alkyl or NO$_2$;
R[3] is H, halogen, —OC$_{1-6}$ alkyl, C$_{1-6}$ alkyl or NO$_2$;
R[4] is H, halogen or C$_{1-6}$ alkyl,
R[5] is H, halogen or C$_{1-6}$ alkyl;
R[6] is H, halogen or C$_{1-6}$ alkyl;
R[7] is H, halogen or C$_{1-6}$ alkyl;
R[8] is H, halogen or —C$_{1-6}$ alkyl;
L is CH$_2$.
R[14] is H, C$_{1-6}$ alkyl or C$_{3-6}$ cycloalkyl; and
R[15] is H, C$_{1-6}$ alkyl or C$_{3-6}$ cycloalkyl.

In another embodiment, the invention provides a compound having Formula I wherein:

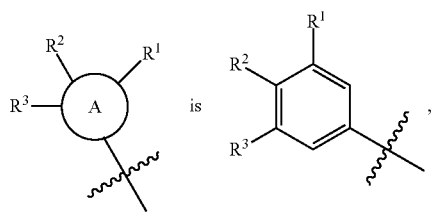

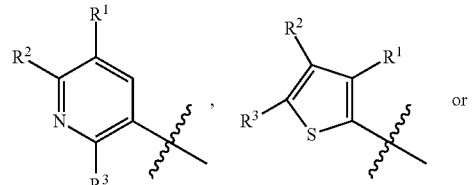

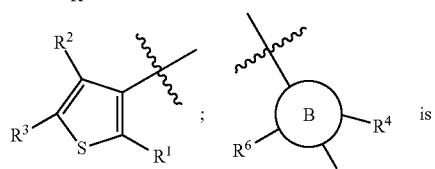

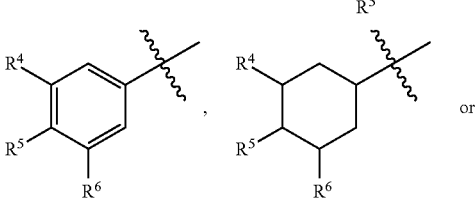

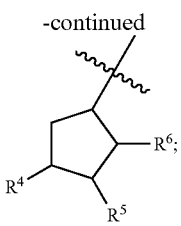

R¹ is H, chloro, bromo, fluoro, methyl, ethyl, methoxy or —NO₂;
R² is H, chloro, trifluoromethyl, methyl or methoxy;
R³ is H, fluoro or methyl;
R⁴ is H or methyl;
R⁵ is H, methyl, chloro or iso-butyl;
R⁶ is H, methyl or chloro;
R⁷ is H;
R⁸ is H;
L is CH₂;
R¹⁴ is H, C$_{1-6}$ alkyl or C$_{3-6}$ cycloalkyl; and
R¹⁵ is H, C$_{1-6}$ alkyl or C$_{3-6}$ cycloalkyl.

The term "alkyl", as used herein, refers to saturated, monovalent hydrocarbon moieties having linear or branched moieties or combinations thereof and containing 1 to 8 carbon atoms. One methylene (—CH₂—) group, of the alkyl can be replaced by oxygen, sulfur, sulfoxide, nitrogen, carbonyl, carboxyl, sulfonyl, or by a divalent C$_{3-6}$ cycloalkyl. Alkyl groups can be substituted by halogen atoms, hydroxyl, cycloalkyl, amino, non-aromatic heterocycles, carboxylic acid, phosphonic acid groups, sulphonic acid groups, phosphoric acid.

The term "cycloalkyl", as used herein, refers to a monovalent or divalent group of 3 to 8 carbon atoms, derived from a saturated cyclic hydrocarbon. Cycloalkyl groups can be monocyclic or polycyclic. Cycloalkyl can be substituted by alkyl groups or halogen atoms.

The term "cycloalkenyl", as used herein, refers to a monovalent or divalent group of 5 to 8 carbon atoms derived from a saturated cycloalkyl having one double bond. Cycloalkenyl groups can be monocyclic or polycyclic. Cycloalkenyl groups can be substituted by alkyl groups or halogen atoms.

The term "halogen", as used herein, refers to an atom of chlorine, bromine, fluorine, iodine.

The term "alkenyl", as used herein, refers to a monovalent or divalent hydrocarbon radical having 2 to 6 carbon atoms, derived from a saturated alkyl, having at least one double bond. C$_{2-6}$ alkenyl can be in the E or Z configuration. Alkenyl groups can be substituted by alkyl groups.

The term "alkynyl", as used herein, refers to a monovalent or divalent hydrocarbon radical having 2 to 6 carbon atoms, derived from a saturated alkyl, having at least one triple bond. Alkynyl groups can be substituted by alkyl groups.

The term "heterocycle" as used herein, refers to a 3 to 10 membered ring, which can be aromatic or non-aromatic, saturated or non-saturated, containing at least one heteroatom selected form O or N or S or combinations of at least two thereof, interrupting the carbocyclic ring structure. The heterocyclic ring can be interrupted by a C═O; the S heteroatom can be oxidized. Heterocycles can be monocyclic or polycyclic. Heterocyclic ring moieties can be substituted by hydroxyl, alkyl groups or halogen atoms.

The term "aryl" as used herein, refers to an organic moiety derived from an aromatic hydrocarbon consisting of a ring containing 6 to 10 carbon atoms by removal of one hydrogen. Aryl groups can be monocyclic or polycyclic. Aryl can be substituted by halogen atoms, —OC$_{1-6}$ alkyl, C$_{1-6}$ alkyl, CN, —C(O)H or —C(O)(C$_{1-6}$ alkyl), NH(C$_{1-6}$ alkyl), NH₂, N(C$_{1-6}$ alkyl) (C$_{1-6}$ alkyl), NO₂ or hydroxyl groups.

The term "hydroxyl" as used herein, represents a group of formula "—OH".

The term "carbonyl" as used herein, represents a group of formula "—C(O)".

The term "carboxyl" as used herein, represents a group of formula "—C(O)O—".

The term "sulfonyl" as used herein, represents a group of formula "—SO₂".

The term "sulfate" as used herein, represents a group of formula "—O—S(O)₂—O—".

The term "carboxylic acid" as used herein, represents a group of formula "—C(O)OH".

The term "sulfoxide" as used herein, represents a group of formula "—S═O".

The term "phosphonic acid" as used herein, represents a group of formula "—P(O)(OH)₂".

The term "phosphoric acid" as used herein, represents a group of formula "—O)P(O)(OH)₂".

The term "sulphonic acid" as used herein, represents a group of formula "—S(O)₂OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
3-{5-[2-(3,4-dimethylphenyl)-1-(3-chlorophenyl)ethyl]-1,2,4-oxadiazol-3-yl}-N-methylpyridin-2-amine;
3-{5-[2-(3,4-dimethylphenyl)-1-(3-bromophenyl)ethyl]-1,2,4-oxadiazol-3-yl}-N-methylpyridin-2-amine;
3-{5-[2-(3,4-dimethylphenyl)-1-(3-fluorophenyl)ethyl]-1,2,4-oxadiazol-3-yl}-N-methylpyridin-2-amine;
3-{5-[2-(3,4-dimethylphenyl)-1-(3-methylphenyl)ethyl]-1,2,4-oxadiazol-3-yl}-N-methylpyridin-2-amine;
3-{5-[2-(3,4-dimethylphenyl)-1-(3-nitrophenyl)ethyl]-1,2,4-oxadiazol-3-yl}-N-methylpyridin-2-amine;
3-{5-[2-(3,4-dimethyl phenyl)-1-(3-methoxyphenyl)ethyl]-1,2,4-oxadiazol-3-yl}-N-methylpyridin-2-amine;
3-{5-[2-(3,4-dimethylphenyl)-1-(3-ethylphenyl)ethyl]-1,2,4-oxadiazol-3-yl}-N-methylpyridin-2-amine;
3-{5-[2-(3,4-dimethylphenyl)-1-phenylethyl]-1,2,4-oxadiazol-3-yl}-N-methylpyridin-2-amine;
3-{5-[2-(3,4-dimethylphenyl)-1-(4-chlorophenyl)ethyl]-1,2,4-oxadiazol-3-yl}-N-methylpyridin-2-amine;
3-{5-[2-(3,4-dimethylphenyl)-1-(4-methoxyphenyl)ethyl]-1,2,4-oxadiazol-3-yl}-N-methylpyridin-2-amine;
3-(5-{2-(3,4-dimethylphenyl)-1-[4-(trifluoromethyl)phenyl]ethyl}-1,2,4-oxadiazol-3-yl)-N-methylpyridin-2-amine;
3-{5-[1-(3-chlorophenyl)-2-phenylethyl]-1,2,4-oxadiazol-3-yl}-N-methylpyridin-2-amine;
3-{5-[1-(4-chlorophenyl)-2-phenylethyl]-1,2,4-oxadiazol-3-yl}-N-methylpyridin-2-amine;
3-{5-[1-(4-chlorophenyl)-2-(3,4-dichlorophenyl)ethyl]-1,2,4-oxadiazol-3-yl}-N-methylpyridin-2-amine;
3-{5-[1-(3-chlorophenyl)-2-(3-methylphenyl)ethyl]-1,2,4-oxadiazol-3-yl}-N-methylpyridin-2-amine;
3-{5-[1-(3-chlorophenyl)-2-(4-methylphenyl)ethyl]-1,2,4-oxadiazol-3-yl}-N-methylpyridin-2-amine;
3-{5-[1-(3-chlorophenyl)-2-(4-isobutylphenyl)ethyl]-1,2,4-oxadiazol-3-yl}-N-methylpyridin-2-amine;
3-{5-[1-(5-chloropyridin-3-yl)-2-(3,4-dimethylphenyl)ethyl]-1,2,4-oxadiazol-3-yl}-N-methylpyridin-2-amine;

3-{5-[1-(6-chloropyridin-3-yl)-2-(3,4-dimethylphenyl)
ethyl]-1,2,4-oxadiazol-3-yl}-N-methylpyridin-2-amine;

3-{5-[1-(6-chloropyridin-3-yl)-2-(3,5-dimethylphenyl)
ethyl]-1,2,4-oxadiazol-3-yl}-N-methylpyridin-2-amine;

3-{5-[1-(3-chlorophenyl)-2-cyclohexylethyl]-1,2,4-oxadiazol-3-yl}-N-methylpyridin-2-amine;

3-{5-[1-(3-chlorophenyl)-2-cyclopentylethyl]-1,2,4-oxadiazol-3-yl}-N-methylpyridin-2-amine;

N-methyl-3-(5-(1-(thiophen-3-yl)-2-(p-tolyl)ethyl)-1,2,4-oxadiazol-3-yl)pyridin-2-amine;

3-(5-(2-(3,4-dimethylphenyl)-1-(thiophen-3-yl)ethyl)-1,2,4-oxadiazol-3-yl)-N-methylpyridin-2-amine;

3-(5-(1-(3,5-difluorophenyl)-2-(3,4-dimethylphenyl)ethyl)-1,2,4-oxadiazol-3-yl)-N-methylpyridin-2-amine;

3-(5-(1,2-diphenylethyl)-1,2,4-oxadiazol-3-yl)-N-methylpyridin-2-amine 3-(5-(2-(3,4-dimethylphenyl)-1-(3,5-dimethylphenyl)ethyl)-1,2,4-oxadiazol-3-yl)-N-methylpyridin-2-amine;

N-methyl-3-(5-(1-(thiophen-2-yl)-2-(p-tolyl)ethyl)-1,2,4-oxadiazol-3-yl)pyridin-2-amine;

3-(5-(2-(3,4-dimethylphenyl)-1-(thiophen-2-yl)ethyl)-1,2,4-oxadiazol-3-yl)-N-methylpyridin-2-amine;

3-{5-[1-(3,5-difluorophenyl)-2-(3,4-dimethylphenyl)ethyl]-1,2,4-oxadiazol-3-yl}-N-ethylpyridin-2-amine;

3-{5-[1-(3,5-difluorophenyl)-2-(3,4-dimethylphenyl)ethyl]-1,2,4-oxadiazol-3-yl}-N-propylpyridin-2-amine;

N-cyclobutyl-3-{5-[1-(3,5-difluorophenyl)-2-(3,4-dimethylphenyl)ethyl]-1,2,4-oxadiazol-3-yl}pyridin-2-amine;

3-{5-[1-(3,5-difluorophenyl)-2-(3,4-dimethylphenyl)ethyl]-1,2,4-oxadiazol-3-yl}-N,N-dimethylpyridin-2-amine.

Some compounds of Formula I and some of their intermediates have at least one stereogenic center in their structure. This stereogenic center may be present in an R or S configuration, said R and S notation is used in correspondence with the rules described in Pure Appli. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic, hydroxyacetic, propanoic, lactic, pyruvic, malonic, fumaric acid, maleic acid, oxalic acid, tartaric acid, succinic acid, malic acid, ascorbic acid, benzoic acid, tannic acid, pamoic acid, citric, methylsulfonic, ethanesulfonic, benzenesulfonic, formic and the like (Handbook of Pharmaceutical Salts, P. Heinrich Stahal & Camille G. Wermuth (Eds), Verlag Helvetica Chemica Acta-Zürich, 2002, 329-345).

Compounds of Formula I and their salts can be in the form of a solvate, which is included within the scope of the present invention. Such solvates include for example hydrates, alcoholates and the like.

With respect to the present invention reference to a compound or compounds, is intended to encompass that compound in each of its possible isomeric forms and mixtures thereof unless the particular isomeric form is referred to specifically.

Compounds according to the present invention may exist in different polymorphic forms. Although not explicitly indicated in the above formula, such forms are intended to be included within the scope of the present invention.

The compounds of the invention are indicated for use in treating or preventing conditions in which there is likely to be a component involving the sphingosine-1-phosphate receptors.

In another embodiment, there are provided pharmaceutical compositions including at least one compound of the invention in a pharmaceutically acceptable carrier.

In a further embodiment of the invention, there are provided methods for treating disorders associated with modulation of sphingosine-1-phosphate receptors. Such methods can be performed, for example, by administering to a subject in need thereof a pharmaceutical composition containing a therapeutically effective amount of at least one compound of the invention.

These compounds are useful for the treatment of mammals, including humans, with a range of conditions and diseases that are alleviated by S1P modulation.

Therapeutic utilities of S1P modulators are:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

In still another embodiment of the invention, there are provided methods for treating disorders associated with modulation of sphingosine-1-phosphate receptors. Such methods can be performed, for example, by administering to a subject in need thereof a therapeutically effective amount of at least one compound of the invention, or any combination thereof, or pharmaceutically acceptable salts, hydrates, solvates, crystal forms and individual isomers, enantiomers, and diastereomers thereof.

The present invention concerns the use of a compound of Formula I or a pharmaceutically acceptable salt thereof, for the manufacture of a medicament for the treatment of:

Ocular Diseases: wet and dry age-related macular degeneration, diabetic retinopathy, retinopathy of prematurity, retinal edema, geographic atrophy, glaucomatous optic neuropathy, chorioretinopathy, hypertensive retinopathy, ocular ischemic syndrome, prevention of inflammation-induced fibrosis in the back of the eye, various ocular inflammatory diseases including uveitis, scleritis, keratitis, and retinal vasculitis;

Systemic vascular barrier related diseases: various inflammatory diseases, including acute lung injury, its prevention, sepsis, tumor metastasis, atherosclerosis, pulmonary edemas, and ventilation-induced lung injury;

Autoimmune diseases and immnuosuppression: rheumatoid arthritis, Crohn's disease, Graves' disease, inflammatory bowel disease, multiple sclerosis, Myasthenia gravis, Psoriasis, ulcerative colitis, antoimmune uveitis, renal ischemia/perfusion injury, contact hypersensitivity, atopic dermititis, and organ transplantation;

Allergies and other inflammatory diseases: urticaria, bronchial asthma, and other airway inflammations including pulmonary emphysema and chronic obstructive pulmonary diseases;

Cardiac functions: bradycardia, congestional heart failure, cardiac arrhythmia, prevention and treatment of atherosclerosis, and ischemia/reperfusion injury;

Wound Healing: scar-free healing of wounds from cosmetic skin surgery, ocular surgery, GI surgery, general surgery, oral injuries, various mechanical, heat and burn injuries, prevention and treatment of photoaging and skin ageing, and prevention of radiation-induced injuries;

Bone formation: treatment of osteoporosis and various bone fractures including hip and ankles;

Anti-nociceptive activity: visceral pain, pain associated with diabetic neuropathy, rheumatoid arthritis, chronic knee and joint pain, tendonitis, osteoarthritis, neuropathic pains;

Anti-fibrosis: ocular, cardiac, hepatic and pulmonary fibrosis, proliferative vitreoretinopathy, cicatricial pemphigoid, surgically induced fibrosis in cornea, conjunctiva and tenon;

Pains and anti-inflammation: acute pain, flare-up of chronic pain, musculo-skeletal pains, visceral pain, pain associated with diabetic neuropathy, rheumatoid arthritis, chronic knee and joint pain, tendonitis, osteoarthritis, bursitis, neuropathic pains;

CNS neuronal injuries: Alzheimer's disease, age-related neuronal injuries;

Organ transplants: renal, corneal, cardiac and adipose tissue transplants.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention compounds may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of sphingosine-1-phosphate receptors. Thus, in further embodiments of the invention, there are provided methods for treating a disorder associated with modulation of sphingosine-1-phosphate receptors. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of formula I according to the invention can be prepared analogously to conventional methods as understood by the person skilled in the art of synthetic organic chemistry. The synthetic scheme set forth below, illustrate how compounds according to the invention can be made.

The following abbreviations are used in the general scheme and in the specific examples:

| | |
|---|---|
| CDI | 1,1'-carbonyl diimidazole |
| EDCl | 1-ethyl-3-(3-dimethylaminopropyl) carbodiimide |
| NBS | N-bromosuccinimide |
| BPO | benzoyl peroxide |
| KOH | potassium hydroxide |
| MeOH | methanol |
| HCl | hydrochloric acid |
| rt | room temperature |
| CDCl3 | deuterated chloroform |
| DMSO-$d_6$ | deuterated dimethyl sulfoxide |
| NaH | sodium hydride |
| THF | tetrahydrofuran |
| NaOEt | sodium ethoxyde |

Acetonitrile "A" (1 eq) and aldehyde "B" (1 eq) were reacted according to the procedure described in Vaccaro, Wayne et al. Journal of Medicinal Chemistry, 1996, 39(8), 1704-1719 to produce the corresponding propanoic acid intermediate. 1,1'-Carbonyl diimidazole (CDI) (2.10 mmol) in THF was added to 1.90 mmol of acid and the mixture was stirred at rt for 30 minutes, then N-hydroxy-2-(methylamino)-3-pyridine carboximidamide (CAS 801303-19-5) (1.9 mmol) was added and the resulting solution was stirred at rt for 16 hours.

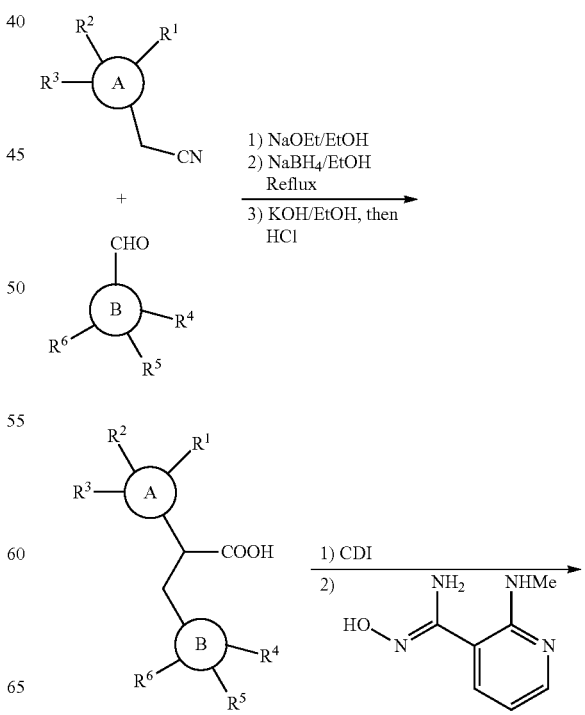

-continued

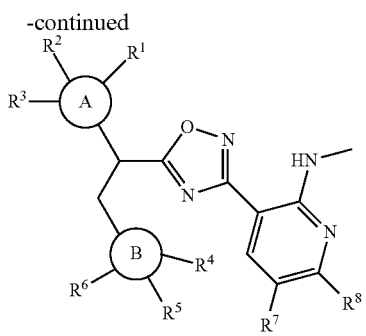

L = CH$_2$
R$^{14}$ is H and R$^{15}$ is methyl
Formula I

The reaction solution was then transferred to a microwave reaction vessel and heated at 150° C. for 20 min under microwave conditions. After cooling at room temperature (rt), the solvent was removed under reduced pressure. The pyridine derivative was isolated by medium pressure liquid chromatography (MPLC) using 5 to 10% ethyl acetate in hexane.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms. Unless it is specifically noted otherwise, the scope of the present invention includes all enantiomers, diastereomers and racemic mixtures. Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2$H (or D) in place of hyrdrogen $^1$H (or H) or use of $^{13}$C enriched material in place of $^{12}$C and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

The following examples are for illustrative purposes only and are not intended, nor should they be construed as limiting the invention in any manner. Those skilled in the art will appreciate that variations and modifications of the following examples can be made without exceeding the spirit or scope of the invention.

As will be evident to those skilled in the art, individual isomeric forms can be obtained by separation of mixtures thereof in conventional manner. For example, in the case of diastereoisomeric isomers, chromatographic separation may be employed.

Compound names were generated with ACD version 8.

In general, characterization of the compounds is performed according to the following methods: Proton nuclear magnetic resonance ($^1$H NMR) spectra were recorded on a Varian 300 or 600 MHz spectrometer in deuterated solvent. Chemical shifts were reported as δ (delta) values in parts per million (ppm) relative to tetramethylsilane (TMS) as an internal standard (0.00 ppm) and multiplicities were reported as s, singlet; d, doublet; t, triplet; q, quartet; m, multiplet; br, broad. Data were reported in the following format: chemical shift (multiplicity, coupling constant(s) J in hertz (Hz), integrated intensity).

All the reagents, solvents, catalysts for which the synthesis is not described are purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on an Teledyne-ISCO CombiFlash with a silica column, unless noted otherwise.

The following synthetic schemes illustrate how compounds according to the invention can be made. Those skilled in the art will be routinely able to modify and/or adapt the following schemes to synthesize any compound of the invention covered by Formula I.

Example 1

Compound 1

N-methyl-3-(5-(1-(thiophen-3-yl)-2-(p-tolyl)ethyl)-1,2,4-oxadiazol-3-yl)pyridin-2-amine

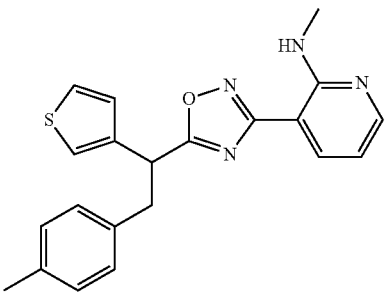 [SMILES: CNc1ncccc1-c1noc(C(Cc2ccc(C)cc2)c2ccsc2)n1]

2-(Thiophen-3-yl)-3-(p-tolyl)propanoic acid was obtained from commercially available 2-(thiophen-3-yl)acetonitrile (10.00 g, 81.18 mmol), 4-tolylaldehyde (10.00 g, 83.23 mmol) sodium ethoxide (20 w/v % in ethanol, 50.00 mL), sodium borohydride (5.00 g, 131.58 mmol) and potassium hydride (5.00 g, 89.11 mmol) according to the protocols as outlined in Vaccaro, Wayne et al. Journal of Medicinal Chemistry, 1996, 39(8), 1704-1719. This acid was used in the next synthetic step without further purification. Crude 2-(thiophen-3-yl)-3-(p-tolyl)propanoic acid (, 2.40 g, 9.74 mmol), carbonyl diimidazole (1.90 g, 11.73 mmol) and N-hydroxy-2-(methylamino)-3-pyridinecarboximidamide (1.66 g, 10.00 mmol) reacted according to the general procedure described above.

$^1$H NMR (300 MHz, DMSO-d$_6$) δ ppm 2.19 (s, 3H), 2.99 (d, J=4.69 Hz, 3H), 3.33-3.38 (m, 1H), 3.43-3.51 (m, 1H), 4.98 (t, J=8.06 Hz, 1H), 6.71 (dd, J=7.47, 4.83 Hz, 1H), 6.91-7.04 (m, 3H), 7.05-7.14 (m, 2H), 7.15-7.28 (m, 1H), 7.40-7.62 (m, 2H), 8.18 (dd, J=7.62, 1.76 Hz, 1H), 8.26 (dd, J=4.83, 1.90 Hz, 1H).

Compounds 2 through 34 were prepared from the carboxylic acid intermediate obtained from the corresponding acetonitrile derivative, the corresponding aldehyde derivative and the corresponding pyridinecarboximidamide in a similar manner to the procedure described in Example 1 in the general procedure described above. The carboxylic acid intermediate and the results are tabulated below in Table 1.

TABLE 1

| Comp No. | IUPAC name | Carboxylic acid intermediate | ¹H NMR δ (ppm) for Compound |
| --- | --- | --- | --- |
| 2 | 3-{5-[2-(3,4-dimethylphenyl)-1-(3-chlorophenyl)ethyl]-1,2,4-oxadiazol-3-yl}-N-methylpyridin-2-amine | 2-(3-chlorophenyl)-3-(3,4-dimethylphenyl) propanoic acid | ¹H NMR (300 MHz, CD₃OD) δ ppm 2.15 (s, 6 H) 3.02-3.07 (m, 3 H) 3.24-3.32 (m, 1 H) 3.52 (dd, J = 13.63, 8.35 Hz, 1 H) 4.69 (t, J = 8.06 Hz, 1 H) 6.71 (dd, J = 7.62, 4.98 Hz, 1 H) 6.80-6.85 (m, 1 H) 6.90-6.96 (m, 2 H) 7.26-7.33 (m, 3 H) 7.40-7.42 (m, 1 H) 8.19 (dd, J = 4.98, 2.05 Hz, 1 H) 8.34 (dd, J = 7.62, 1.76 Hz, 1 H) |
| 3 | 3-{5-[2-(3,4-dimethylphenyl)-1-(3-bromophenyl)ethyl]-1,2,4-oxadiazol-3-yl}-N-methylpyridin-2-amine | 2-(3-bromophenyl)-3-(3,4-dimethylphenyl) propanoic acid | ¹H NMR (300 MHz, CD₃OD) δ ppm 2.15 (s, 6 H) 3.03-3.08 (m, 3 H) 3.23-3.31 (m, 1 H) 3.52 (dd, J = 13.63, 8.35 Hz, 1 H) 4.68 (t, J = 8.06 Hz, 1 H) 6.71 (dd, J = 7.62, 4.98 Hz, 1 H) 6.80-6.86 (m, 1 H) 6.89-6.96 (m, 2 H) 7.20-7.27 (m, 1 H) 7.36 (d, J = 7.62 Hz, 1 H) 7.43 (d, J = 7.62 Hz, 1 H) 7.56 (s, 1 H) 8.19 (dd, J = 4.98, 1.76 Hz, 1 H) 8.34 (dd, J = 7.62, 1.76 Hz, 1 H) |
| 4 | 3-{5-[2-(3,4-dimethylphenyl)-1-(3-fluorophenyl)ethyl]-1,2,4-oxadiazol-3-yl}-N-methylpyridin-2-amine | 2-(3-fluorophenyl)-3-(3,4-dimethylphenyl) propanoic acid | ¹H NMR (300 MHz, CD₃OD) δ ppm 2.14 (s, 6 H) 3.04-3.07 (m, 3 H) 3.24-3.32 (m, 1 H) 3.52 (dd, J = 13.77, 8.50 Hz, 1 H) 4.70 (t, J = 7.91 Hz, 1 H) 6.71 (dd, J = 7.62, 4.98 Hz, 1 H) 6.81-6.86 (m, 1 H) 6.90-6.98 (m, 2 H) 6.99-7.04 (m, 1 H) 7.11-7.22 (m, 2 H) 7.28-7.39 (m, 1 H) 8.19 (dd, J = 4.98, 2.05 Hz, 1 H) 8.34 (dd, J = 7.62, 1.76 Hz, 1 H) |

TABLE 1-continued

| Comp No. | IUPAC name | Carboxylic acid intermediate | $^1$H NMR δ (ppm) for Compound |
| --- | --- | --- | --- |
| 5 | 3-{5-[2-(3,4-dimethylphenyl)-1-(3-methylphenyl)ethyl]-1,2,4-oxadiazol-3-yl}-N-methylpyridin-2-amine | 2-(3-methylphenyl)-3-(3,4-dimethylphenyl) propanoic acid | $^1$H NMR (300 MHz, CD$_3$OD) δ ppm 2.15 (s, 6 H) 2.31 (s, 3 H) 3.04-3.08 (m, 3 H) 3.24-3.32 (m, 1 H) 3.53 (dd, J = 13.48, 8.79 Hz, 1 H) 4.61 (dd, J = 8.79, 7.33 Hz, 1 H) 6.72 (dd, J = 7.62, 4.98 Hz, 1 H) 6.81-6.88 (m, 1 H) 6.89-6.96 (m, 2 H) 7.05-7.11 (m, 1 H) 7.14-7.24 (m, 3 H) 8.19 (dd, J = 4.98, 1.76 Hz, 1 H) 8.34 (dd, J = 7.62, 2.05 Hz, 1 H) |
| 6 | 3-{5-[2-(3,4-dimethylphenyl)-1-(3-nitrophenyl)ethyl]-1,2,4-oxadiazol-3-yl}-N-methylpyridin-2-amine | 2-(3-nitrophenyl)-3-(3,4-dimethylphenyl) propanoic acid | $^1$H NMR (300 MHz, CD$_3$OD) δ ppm 2.14 (s, 6 H) 3.03-3.08 (m, 3 H) 3.32-3.39 (m, 1 H) 3.58 (dd, J = 13.63, 8.06, 1 H) 4.89 (t, J = 8.01 Hz, 1 H) 6.71 (dd, J = 7.62, 4.98 Hz, 1 H) 6.80-6.86 (m, 1 H) 6.90-6.95 (m, 2 H) 7.52-7.60 (m, 1 H) 7.79 (d, J = 7.91 Hz, 1 H) 8.11-8.17 (m, 1 H) 8.19 (dd, J = 4.98, 1.76 Hz, 1 H) 8.28 (s, 1 H) 8.34 (dd, J = 7.33, 1.76 Hz, 1 H) |
| 7 | 3-{5-[2-(3,4-dimethylphenyl)-1-(3-methoxyphenyl)ethyl]-1,2,4-oxadiazol-3-yl}-N-methylpyridin-2-amine | 2-(3-methoxyphenyl)-3-(3,4-dimethylphenyl) propanoic acid | $^1$H NMR (300 MHz, CD$_3$OD) δ ppm 2.13 (s, 6 H) 3.02-3.06 (m, 3 H) 3.23-3.30 (m, 1 H) 3.50 (dd, J = 13.63, 8.64 Hz, 1 H) 3.74 (s, 3 H) 4.61 (dd, J = 8.50, 7.62 Hz, 1 H) 6.68 (dd, J = 7.62, 4.98 Hz, 1 H) 6.79-6.85 (m, 2 H) 6.89-6.96 (m, 4 H) 7.19-7.26 (m, 1 H) 8.17 (dd, J = 4.98, 1.76 Hz, 1 H) 8.32 (dd, J = 7.47, 1.90 Hz, 1 H) |

TABLE 1-continued

| Comp No. | IUPAC name | Carboxylic acid intermediate | ¹H NMR δ (ppm) for Compound |
|---|---|---|---|
| 8 | 3-{5-[2-(3,4-dimethylphenyl)-1-(3-ethylphenyl)ethyl]-1,2,4-oxadiazol-3-yl}-N-methylpyridin-2-amine | 2-(3-ethylphenyl)-3-(3,4-dimethylphenyl) propanoic acid | ¹H NMR (300 MHz, CD$_3$OD) δ ppm 1.17 (t, J = 7.62 Hz, 3 H) 2.13 (s, 6 H) 2.59 (q, J = 7.62 Hz, 2 H) 3.01-3.08 (m, 3 H) 3.22-3.31 (m, 1 H) 3.52 (dd, J = 13.63, 8.64 Hz, 1 H) 4.61 (t, J = 7.91 Hz, 1 H) 6.70 (dd, J = 7.62, 4.98 Hz, 1 H) 6.79-6.85 (m, 1 H) 6.86-6.95 (m, 2 H) 7.10 (d, J = 6.74 Hz, 1 H) 7.13-7.27 (m, 3 H) 8.15-8.20 (m, 1 H) 8.33 (dd, J = 7.62, 1.76 Hz, 1 H). |
| 9 | 3-{5-[2-(3,4-dimethylphenyl)-1-phenylethyl]-1,2,4-oxadiazol-3-yl}-N-methylpyridin-2-amine | 3-(3,4-dimethylphenyl)-2-phenylpropanoic acid | ¹H NMR (300 MHz, CD$_3$OD) δ ppm 2.14 (s, 6 H) 3.05 (s, 3 H) 3.24-3.31 (m, 1 H) 3.53 (dd, J = 13.63, 8.64 Hz, 1 H) 4.65 (dd, J = 8.50, 7.33 Hz, 1 H) 6.70 (dd, J = 7.62, 4.98 Hz, 1 H) 6.80-6.85 (m, 1 H) 6.89-6.94 (m, 2 H) 7.24-7.40 (m, 5 H) 8.18 (dd, J = 4.98, 2.05 Hz, 1 H) 8.33 (dd, J = 7.62, 1.76 Hz, 1 H). |
| 10 | 3-{5-[2-(3,4-dimethylphenyl)-1-(4-chlorophenyl)ethyl]-1,2,4-oxadiazol-3-yl}-N-methylpyridin-2-amine | 2-(4-chlorophenyl)-3-(3,4-dimethylphenyl) propanoic acid | ¹H NMR (300 MHz, CD$_3$OD) δ ppm 2.14 (s, 6 H) 3.03-3.07 (m, 3 H) 3.22-3.31 (m, 1 H) 3.52 (dd, J = 13.77, 8.20 Hz, 1 H) 4.67 (t, J = 8.06 Hz, 1 H) 6.71 (dd, J = 7.62, 4.98 Hz, 1 H) 6.79-6.84 (m, 1 H) 6.89-6.95 (m, 2 H) 7.28-7.38 (m, 4 H) 8.19 (dd, J = 4.98, 1.76 Hz, 1 H) 8.34 (dd, J = 7.62, 2.05 Hz, 1 H) |

TABLE 1-continued

| Comp No. | IUPAC name | Carboxylic acid intermediate | $^1$H NMR δ (ppm) for Compound |
|---|---|---|---|
| 11 | 3-{5-[2-(3,4-dimethylphenyl)-1-(4-methoxyphenyl)ethyl]-1,2,4-oxadiazol-3-yl}-N-methylpyridin-2-amine | 2-(4-methoxyphenyl)-3-(3,4-dimethylphenyl)propanoic acid | $^1$H NMR (300 MHz, CD$_3$OD) δ ppm 2.14 (s, 6 H) 3.04-3.09 (m, 3 H) 3.20-3.29 (m, 1 H) 3.50 (dd, J = 13.48, 8.50 Hz, 1 H) 3.75 (s, 3 H) 4.59 (t, J = 8.06 Hz, 1 H) 6.71 (dd, J = 7.62, 4.98 Hz, 1 H) 6.78-6.96 (m, 5 H) 7.24-7.33 (m, 2 H) 8.18 (dd, J = 4.98, 1.76 Hz, 1 H) 8.34 (dd, J = 7.62, 2.05 Hz, 1 H) |
| 12 | 3-(5-{2-(3,4-dimethylphenyl)-1-[4-(trifluoromethyl)phenyl]ethyl}-1,2,4-oxadiazol-3-yl)-N-methylpyridin-2-amine | 2-(4-trifluoromethylphenyl)-3-(3,4-dimethylphenyl)propanoic acid | $^1$H NMR (300 MHz, CD$_3$OD) δ ppm 2.14 (s, 3 H) 2.15 (s, 3 H) 3.05-3.08 (m, 3 H) 3.28-3.31 (m, 1H) 3.57 (dd, J = 13.77, 8.20 Hz, 1 H) 4.80 (t, J = 7.91 Hz, 1 H) 6.72 (dd, J = 7.62, 4.98 Hz, 1 H) 6.80-6.86 (m, 1 H) 6.89-6.96 (m, 2 H) 7.60 (m, 4 H) 8.19 (dd, J = 4.98, 1.76 Hz, 1 H) 8.35 (dd, J = 7.62, 1.76 Hz, 1 H) |
| 13 | 3-{5-[1-(3-chlorophenyl)-2-phenylethyl]-1,2,4-oxadiazol-3-yl}-N-methylpyridin-2-amine | 2-(3-chlorophenyl)-3-phenylpropanoic acid | $^1$H NMR (300 MHz, CD$_3$OD) δ ppm 3.04-3.07 (m, 3 H) 3.37 (dd, J = 13.77, 7.91 Hz, 1 H) 3.61 (dd, J = 13.77, 8.20 Hz, 1 H) 4.73 (t, J = 7.91 Hz, 1 H) 6.71 (dd, J = 7.62, 4.98 Hz, 1 H) 7.12-7.22 (m, 5 H) 7.26-7.33 (m, 3 H) 7.41 (m, 1 H) 8.19 (dd, J = 4.98, 1.76 Hz, 1 H) 8.34 (dd, J = 7.62, 2.05 Hz, 1 H) |

TABLE 1-continued

| Comp No. | IUPAC name | Carboxylic acid intermediate | ¹H NMR δ (ppm) for Compound |
|---|---|---|---|
| 14 | 3-{5-[1-(4-chlorophenyl)-2-phenylethyl]-1,2,4-oxadiazol-3-yl}-N-methylpyridin-2-amine | 2-(4-chlorophenyl)-3-phenylpropanoic acid | ¹H NMR (300 MHz, CD$_3$OD) δ ppm 3.05-3.09 (m, 3 H) 3.37 (dd, J = 13.77, 7.91 Hz, 1 H) 3.61 (dd, J = 13.77, 8.20 Hz, 1 H) 4.73 (t, J = 7.91 Hz, 1 H) 6.74 (dd, J = 7.62, 4.98 Hz, 1 H) 7.12-7.22 (m, 5 H) 7.31-7.38 (m, 4 H) 8.18-8.22 (m, 1 H) 8.34 (dd, J = 7.62, 2.05 Hz, 1 H) |
| 15 | 3-{5-[1-(4-chlorophenyl)-2-(3,4-dichlorophenyl)ethyl]-1,2,4-oxadiazol-3-yl}-N-methylpyridin-2-amine | 2-(4-chlorophenyl)-3-(3,4-dichlorophenyl)propanoic acid | ¹H NMR (300 MHz, CD$_3$OD) δ ppm 3.06-3.09 (m, 3 H) 3.38 (dd, J = 13.77, 8.20 Hz, 1 H) 3.62 (dd, J = 13.77, 7.62 Hz, 1 H) 4.75 (t, J = 8.06 Hz, 1 H) 6.74 (dd, J = 7.62, 4.98 Hz, 1 H) 7.07 (dd, J = 8.20, 2.05 Hz, 1 H) 7.32-7.39 (m, 6 H) 8.21 (dd, J = 4.98, 2.05 Hz, 1 H) 8.37 (dd, J = 7.62, 1.76 Hz, 1 H) |
| 16 | 3-{5-[1-(3-chlorophenyl)-2-(3-methylphenyl)ethyl]-1,2,4-oxadiazol-3-yl}-N-methylpyridin-2-amine | 2-(3-chlorophenyl)-3-(3-methylphenyl)propanoic acid | ¹H NMR (300 MHz, CD$_3$OD) δ ppm 2.23 (s, 3 H) 3.08 (s, 3 H) 3.31-3.39 (m, 1 H) 3.58 (dd, J = 13.77, 8.20 Hz, 1 H) 4.73 (t, J = 7.91 Hz, 1 H) 6.75 (dd, J = 7.62, 4.98 Hz, 1 H) 6.90-7.00 (m, 3 H) 7.04-7.11 (m, 1 H) 7.27-7.34 (m, 3 H) 7.42 (s, 1 H) 8.20 (dd, J = 4.98, 2.05 Hz, 1 H) 8.38 (dd, J = 7.62, 1.76 Hz, 1 H) |

TABLE 1-continued

| Comp No. | IUPAC name | Carboxylic acid intermediate | $^1$H NMR δ (ppm) for Compound |
|---|---|---|---|
| 17 | 3-{5-[1-(3-chlorophenyl)-2-(4-isobutylphenyl)ethyl]-1,2,4-oxadiazol-3-yl}-N-methylpyridin-2-amine | 2-(3-chlorophenyl)-3-(4-isobutylphenyl) propanoic acid | $^1$H NMR (300 MHz, CD$_3$OD) δ ppm 0.83 (d, J = 6.74 Hz, 6 H) 1.77 (dt, J = 13.48, 6.74 Hz, 1 H) 2.38 (d, J = 7.33 Hz, 2 H) 3.06 (s, 3 H) 3.32-3.39 (m, 1 H) 3.58 (dd, J = 13.48, 8.20 Hz, 1 H) 4.70 (t, J = 8.06 Hz, 1 H) 6.72 (dd, J = 7.62, 4.98 Hz, 1 H) 6.93-7.07 (m, 4 H) 7.25-7.35 (m, 3 H) 7.38 (s, 1 H) 8.19 (dd, J = 4.98, 1.76 Hz, 1 H) 8.35 (dd, J = 7.47, 1.90 Hz, 1 H) |
| 18 | 3-{5-[1-(5-chloropyridin-3-yl)-2-(3,4-dimethylphenyl)ethyl]-1,2,4-oxadiazol-3-yl}-N-methylpyridin-2-amine | 2-(5-chloropyridin-3-yl)-3-(3,4-dimethylphenyl) propanoic acid | $^1$H NMR (300 MHz, CD$_3$OD) δ ppm 2.15 (s, 6 H) 3.04-3.09 (m, 3 H) 3.28-3.36 (m, 1 H) 3.57 (dd, J = 13.63, 7.76 Hz, 1 H) 4.86 (t, J = 7.91 Hz, 1 H) 6.71 (dd, J = 7.62, 4.98 Hz, 1 H) 6.78-6.84 (m, 1 H) 6.88-6.98 (m, 2 H) 7.96 (t, J = 2.05 Hz, 1 H) 8.20 (dd, J = 4.98, 1.76 Hz, 1 H) 8.33 (dd, J = 7.62, 1.76 Hz, 1 H) 8.45 (dd, J = 7.33, 2.05 Hz, 2 H) |
| 19 | 3-{5-[1-(6-chloropyridin-3-yl)-2-(3,4-dimethylphenyl)ethyl]-1,2,4-oxadiazol-3-yl}-N-methylpyridin-2-amine | 2-(6-chloropyridin-3-yl)-3-(3,4-dimethylphenyl) propanoic acid | $^1$H NMR (300 MHz, CD$_3$OD) δ ppm 2.16 (s, 6 H) 3.04-3.08 (m, 3 H) 3.25-3.33 (m, 1 H) 3.57 (dd, J = 13.63, 7.47 Hz, 1 H) 4.82 (t, J = 7.91 Hz, 1 H) 6.73 (dd, J = 7.62, 4.98 Hz, 1 H) 6.82 (d, J = 7.91 Hz, 1 H) 6.89-6.98 (m, 2 H) 7.43 (d, J = 8.50 Hz, 1 H) 7.91 (dd, J = 8.50, 2.64 Hz, 1 H) 8.21 (dd, J = 4.98, 2.05 Hz, 1 H) 8.30 (d, J = 2.34 Hz, 1 H) 8.35 (dd, J = 7.77, 1.90 Hz, 1 H) |

TABLE 1-continued

| Comp No. | IUPAC name | Carboxylic acid intermediate | $^1$H NMR δ (ppm) for Compound |
|---|---|---|---|
| 20 | 3-{5-[1-(6-chloropyridin-3-yl)-2-(3,5-dimethylphenyl)ethyl]-1,2,4-oxadiazol-3-yl}-N-methylpyridin-2-amine | 2-(6-chloropyridin-3-yl)-3-(3,5-dimethylphenyl)propanoic acid | $^1$H NMR (300 MHz, CD$_3$OD) δ ppm 2.20 (s, 3 H) 2.23 (s, 3 H) 3.03-3.07 (m, 3 H) 3.28-3.35 (m, 1 H) 3.62 (dd, J = 13.77, 7.62 Hz, 1 H) 4.78 (t, J = 7.91 Hz, 1 H) 6.71 (dd, J = 7.62, 4.98 Hz, 1 H) 6.81 (s, 2 H) 6.93 (s, 1 H) 7.42 (d, J = 8.20 Hz, 1 H) 7.89 (dd, J = 8.20, 2.64 Hz, 1 H) 8.19 (dd, J = 4.98, 1.76 Hz, 1 H) 8.28 (d, J = 2.34 Hz, 1 H) 8.34 (dd, J = 7.47, 1.90 Hz, 1 H) |
| 21 | 3-{5-[1-(3-chlorophenyl)-2-cyclohexylethyl]-1,2,4-oxadiazol-3-yl}-N-methylpyridin-2-amine | 2-(3-chlorophenyl)-3-cyclohexylpropanoic acid | $^1$H NMR (300 MHz, CD$_3$OD) δ ppm 0.92-1.30 (m, 6 H) 1.56-1.84 (m, 5 H) 1.92-2.04 (m, 1 H) 2.10-2.25 (m, 1 H) 3.01-3.11 (m, 3 H) 4.53 (t, J = 7.91 Hz, 1 H) 6.70 (dd, J = 7.62, 4.98 Hz, 1 H) 7.25-7.37 (m, 3 H) 7.45 (s, 1 H) 8.18 (dd, J = 4.98, 1.76 Hz, 1 H) 8.33 (dd, J = 7.62, 1.76 Hz, 1 H) |
| 22 | 3-{5-[1-(3-chlorophenyl)-2-cyclopentylethyl]-1,2,4-oxadiazol-3-yl}-N-methylpyridin-2-amine | 2-(3-chlorophenyl)-3-cyclopentylpropanoic acid | $^1$H NMR (300 MHz, CD$_3$OD) δ ppm 1.05-1.15 (m, 2 H) 1.43-1.84 (m, 7 H) 2.08-2.20 (m, 1 H) 2.23-2.35 (m, 1 H) 3.02-3.10 (m, 3 H) 4.43 (t, J = 7.91 Hz, 1 H) 6.71 (dd, J = 7.62, 4.98 Hz, 1 H) 7.26-7.39 (m, 3 H) 7.46 (d, J = 0.88 Hz, 1 H) 8.19 (dd, J = 4.98, 1.76 Hz, 1 H) 8.34 (dd, J = 7.62, 1.76 Hz, 1 H). |

TABLE 1-continued

| Comp No. | IUPAC name | Carboxylic acid intermediate | $^1$H NMR δ (ppm) for Compound |
|---|---|---|---|
| 23 | 3-(5-(1-(3,5-difluorophenyl)-2-(3,4-dimethylphenyl)ethyl)-1,2,4-oxadiazol-3-yl)-N-methylpyridin-2-amine | 2-(3,5-difluorophenyl)-3-(3,4-dimethylphenyl)propanoic acid | : $^1$H NMR (300 MHz, CDCl$_3$) δ ppm 2.18 (s, 6 H), 3.13 (d, J = 4.69 Hz, 3 H), 3.28 (d, J = 7.33 Hz, 1 H), 3.51 (d, J = 8.50 Hz, 1 H), 4.37-4.68 (m, 1 H), 6.54-6.84 (m, 3 H), 6.86-7.10 (m, 5 H), 8.22-8.42 (m, 2 H). |
| 24 | 3-(5-(1,2-diphenylethyl)-1,2,4-oxadiazol-3-yl)-N-methylpyridin-2-amine | 2,3-diphenylpropanoic acid | $^1$H NMR (300 MHz, DMSO-d$_6$) δ ppm 2.98 (d, J = 4.69 Hz, 3 H), 3.37 (dd, J = 13.63, 7.76 Hz, 1 H), 3.59 (dd, J = 13.77, 8.50 Hz, 1 H), 4.91 (t, J = 8.06 Hz, 1 H), 6.72 (dd, J = 7.62, 4.98 Hz, 1 H), 6.97 (d, J = 4.69 Hz, 1 H), 7.06-7.18 (m, 1 H), 7.18-7.22 (m, 3 H), 7.23-7.37 (m, 3 H), 7.39-7.47 (m, 2 H), 8.20 (dd, J = 7.62, 2.05 Hz, 1 H), 8.26 (dd, J = 4.69, 2.05 Hz, 1 H). |
| 25 | 3-(5-(2-(3,4-dimethylphenyl)-1-(3,5-dimethylphenyl)ethyl)-1,2,4-oxadiazol-3-yl)-N-methylpyridin-2-amine | 2-(3,5-difluorophenyl)-3-(3,4-dimethylphenyl)propanoic acid | $^1$H NMR (300 MHz, DMSO-d$_6$) δ ppm 2.08 (s, 3 H), 2.10 (s, 3 H), 2.22 (s, 6 H), 2.98 (d, J = 4.69 Hz, 3 H), 3.24 (dd, J = 13.92, 6.59 Hz, 1 H), 3.47 (dd, J = 13.77, 9.38 Hz, 1 H), 4.65-4.83 (m, 1 H), 6.70 (dd, J = 7.62, 4.69 Hz, 1 H), 6.86-6.94 (m, 3 H), 6.94-7.00 (m, 1 H), 7.04 (s, 3H), 8.19 (dd, J = 7.62, 1.76 Hz, 1 H), 8.25 (dd, J = 4.83, 1.90 Hz, 1 H). |
| 26 | N-methyl-3-(5-(1-(thiophen-2-yl)-2-(p-tolyl)ethyl)-1,2,4-oxadiazol-3-yl)pyridin-2-amine | 2-(thiophen-2-yl)-3-(p-tolyl)propanoic acid | $^1$H NMR (300 MHz, CDCl$_3$) δ ppm 2.27 (s, 2 H), 3.13 (d, J = 4.69 Hz, 2 H), 3.31-3.47 (m, 1 H), 3.49-3.81 (m, 1 H), 4.87 (t, J = 7.91 Hz, 1 H), 6.66 (dd, J = 7.47, 5.13 Hz, 1 H), 6.83-7.12 (m, 5 H), 7.24 (dd, J = 5.13, 1.03 Hz, 1 H), 8.14-8.41 (m, 2 H). |

TABLE 1-continued

| Comp No. | IUPAC name | Carboxylic acid intermediate | $^1$H NMR δ (ppm) for Compound |
|---|---|---|---|
| 27 | 3-(5-(2-(3,4-dimethylphenyl)-1-(thiophen-2-yl)ethyl)-1,2,4-oxadiazol-3-yl)-N-methylpyridin-2-amine | 3-(3,4-dimethylphenyl)-2-(thiophen-2-yl) propanoic acid | $^1$H NMR (300 MHz, CDCl$_3$) δ ppm 2.18 (s, 6 H), 3.13 (d, J = 4.69 Hz, 3 H), 3.40 (d, J = 6.74 Hz, 1 H), 3.54 (d, J = 8.50 Hz, 1 H), 4.87 (s, 1 H), 6.66 (dd, J = 7.33, 5.27 Hz, 1 H), 6.84 (d, J = 7.62 Hz, 1 H), 6.90-7.13 (m, 5 H), 7.23 (d, J = 4.69 Hz, 1 H), 8.23-8.38 (m, 2 H). |
| 28 | 3-{5-[1-(3-chlorophenyl)-2-(4-methylphenyl)-ethyl]-1,2,4-oxadiazol-3-yl}-N-methylpyridin-2-amine | (3-chlorophenyl)-3-(4-methylphenyl) propanoic acid | $^1$H NMR (300 MHz, CD$_3$OD) δ ppm 2.22 (s, 3 H) 3.01-3.08 (m, 3 H) 3.27-3.34 (m, 1 H) 3.55 (dd, J = 13.77, 8.20 Hz, 1 H) 4.68 (t, J = 8.06 Hz, 1 H) 6.69 (dd, J = 7.62, 4.98 Hz, 1 H) 6.96-7.04 (m, 4 H) 7.24-7.33 (m, 3 H) 7.40 (s, 1 H) 8.17 (dd, J = 4.98, 1.76 Hz, 1 H) 8.32 (dd, J = 7.62, 1.76 Hz, 1 H) |
| 29 | 3-(5-(2-(3,4-dimethylphenyl)-1-(thiophen-3-yl)ethyl)-1,2,4-oxadiazol-3-yl)-N-methylpyridin-2-amine | 3-(3,4-dimethylphenyl)-2-(thiophen-3-yl)propanoic acid | $^1$H NMR (300 MHz, CDCl$_3$) δ ppm 2.17 (s, 7 H), 3.12 (d, J = 4.69 Hz, 3 H), 3.22-3.39 (m, 1 H), 3.42-3.60 (m, 1 H), 4.70 (t, J = 7.77 Hz, 1 H), 6.65 (dd, J = 7.33, 5.27 Hz, 1 H), 6.80 (d, J = 7.33 Hz, 1 H), 6.87 (s, 1 H), 6.96 (d, J = 7.91 Hz, 1 H), 7.02 (d, J = 3.52 Hz, 1 H), 7.09-7.14 (m, 1 H), 7.17 (s, 1 H), 7.29 (dd, J = 4.83, 3.08 Hz, 1 H), 8.20-8.39 (m, 2 H). |

TABLE 1-continued

| Comp No. | IUPAC name | Carboxylic acid intermediate | $^1$H NMR δ (ppm) for Compound |
|---|---|---|---|
| 30 | 3-{5-[2-(3,4-dimethylphenyl)-1-(3-nitrophenyl)ethyl]-1,2,4-oxadiazol-3-yl}-N-methylpyridin-2-amine | 2-(3-nitrophenyl)-3-(3,4-dimethylphenyl) propanoic acid | $^1$H NMR (300 MHz, DMSO-d$_6$) δ ppm 2.09 (s, 5 H), 2.98 (d, J = 4.69 Hz, 3 H), 3.28-3.36 (m, 1 H), 3.45-3.64 (m, 1 H), 5.08 (s, 1 H), 6.72 (dd, J = 7.62, 4.69 Hz, 1 H), 6.82-7.07 (m, 4 H), 7.46-7.69 (m, 2 H), 7.72-7.87 (m, 2 H), 8.10-8.34 (m, 2 H). |
| 31 | 3-{5-[1-(3,5-difluorophenyl)-2-(3,4-dimethylphenyl)ethyl]-1,2,4-oxadiazol-3-yl}-N-ethylpyridin-2-amine | 2-(3,5-difluorophenyl)-3-(3,4-dimethylphenyl) propanoic acid 2-(ethylamino)-N'-hydroxynicotinimidamide | $^1$H NMR (300 MHz, DMSO-d$_6$) δ ppm 1.04-1.21 (m, 3H), 2.09 (s, 3 H), 2.10 (s, 3 H), 3.23-3.37 (m, 1 H), 3.42-3.58 (m, 3 H), 4.00 (q, J = 7.13 Hz, 1 H), 4.99 (t, J = 8.06 Hz, 1 H), 6.71 (dd, J = 7.62, 4.98 Hz, 1 H), 6.83-7.04 (m, 4 H), 7.09-7.29 (m, 3 H), 8.14-8.28 (m, 2 H) |
| 32 | 3-{5-[1-(3,5-difluorophenyl)-2-(3,4-dimethylphenyl)ethyl]-1,2,4-oxadiazol-3-yl}-N-propylpyridin-2-amine | 2-(3,5-difluorophenyl)-3-(3,4-dimethylphenyl) propanoic acid 2-(propylamino)-N'-hydroxynicotinimidamide | $^1$H NMR (300 MHz, DMSO-d$_6$) δ ppm 0.85-0.96 (m, 3H), 1.49-1.65 (m, 2 H), 2.09 (s, 3 H), 2.10 (s, 3 H), 3.24-3.36 (m, 1 H), 3.40-3.56 (m, 3 H), 4.98 (t, J = 8.06 Hz, 1 H), 6.71 (dd, J = 7.62, 4.69 Hz, 1 H), 6.86-7.07 (m, 5 H), 7.11-7.28 (m, 3 H), 8.15-8.27 (m, 2 H) |

TABLE 1-continued

| Comp No. | IUPAC name | Carboxylic acid intermediate | $^1$H NMR δ (ppm) for Compound |
|---|---|---|---|
| 33 | N-cyclobutyl-3-{5-[1-(3,5-difluorophenyl)-2-(3,4-dimethylphenyl)ethyl]-1,2,4-oxadiazol-3-yl}pyridin-2-amine | 2-(3,5-difluorophenyl)-3-(3,4-dimethylphenyl) propanoic acid 2-(cyclobutylamino)-N'-hydroxynicotinimidamide | $^1$H NMR (300 MHz, DMSO-$d_6$) δ ppm 1.57-1.76 (m, 2 H), 1.85 (d, J = 2.93 Hz, 2 H), 2.09 (s, 3 H), 2.10 (s, 3 H), 2.24-2.41 (m, 2 H), 3.26-3.34 (m, 1 H), 3.42-3.58 (m, 1 H), 4.40-4.67 (m, 1 H), 4.99 (s, 1 H), 6.72 (dd, J = 7.62, 4.98 Hz, 1 H), 6.85-6.97 (m, 2 H), 7.00 (s, 1 H), 7.09-7.16 (m, 2 H), 7.23 (dd, J = 8.50, 2.34 Hz, 2 H), 8.12-8.25 (m, 2 H). |
| 34 | 3-{5-[1-(3,5-difluorophenyl)-2-(3,4-dimethylphenyl)ethyl]-1,2,4-oxadiazol-3-yl}-N,N-dimethylpyridin-2-amine | 2-(3,5-difluorophenyl)-3-(3,4-dimethylphenyl) propanoic acid 2-(dimethylamino)-N'-hydroxynicotinimidamide (CAS 1016701-63-5) | $^1$H NMR (300 MHz, DMSO-$d_6$) δ ppm 2.10 (s, 6 H), 2.65 (s, 6 H), 3.25-3.32 (m, 1 H), 3.38-3.54 (m, 1 H), 4.89-5.06 (m, 1 H), 6.79 (dd, J = 7.62, 4.69 Hz, 1 H), 6.96 (d, J = 14.94 Hz, 3 H), 7.08-7.31 (m, 3 H), 7.76 (dd, J = 7.47, 1.90 Hz, 1 H), 8.24 (dd, J = 4.69, 2.05 Hz, 1 H) |

Biological Data

Compounds were synthesized and tested for S1P1 activity using the GTP $\gamma^{35}$S binding assay. These compounds may be assessed for their ability to activate or block activation of the human S1P1 receptor in cells stably expressing the S1P1 receptor.

GTP $\gamma^{35}$S binding was measured in the medium containing (mM) HEPES 25, pH 7.4, $MgCl_2$ 10, NaCl 100, dithitothreitol 0.5, digitonin 0.003%, 0.2 nM GTP $\gamma^{35}$S, and 5 μg membrane protein in a volume of 150 μl. Test compounds were included in the concentration range from 0.08 to 5,000 nM unless indicated otherwise. Membranes were incubated with 100 μM 5'-adenylylimmidodiphosphate for 30 min, and subsequently with 10 μM GDP for 10 min on ice. Drug solutions and membrane were mixed, and then reactions were initiated by adding GTP $\gamma^{35}$S and continued for 30 min at 25° C. Reaction mixtures were filtered over Whatman GF/B filters under vacuum, and washed three times with 3 mL of ice-cold buffer (HEPES 25, pH7.4, $MgCl_2$ 10 and NaCl-100). Filters were dried and mixed with scintillant, and counted for $^{35}$S activity using a β-counter. Agonist-induced GTP $\gamma^{35}$S binding was obtained by subtracting that in the absence of agonist. Binding data were analyzed using a non-linear regression method. In case of antagonist assay, the reaction mixture contained 10 nM S1P in the presence of test antagonist at concentrations ranging from 0.08 to 5000 nM.

Table 2 shows activity potency: S1P1 receptor from GTP $\gamma^{35}$S: nM, ($EC_{50}$).

Activity potency: S1P1 receptor from GTP $\gamma^{35}$S: nM, ($EC_{50}$),

TABLE 2

| IUPAC name | S1P1 $EC_{50}$ (nM) |
|---|---|
| 3-{5-[2-(3,4-dimethylphenyl)-1-(4-methoxyphenyl)ethyl]-1,2,4-oxadiazol-3-yl}-N-methylpyridin-2-amine | 1330 |
| 3-{5-[1-(3-chlorophenyl)-2-(4-isobutylphenyl)ethyl]-1,2,4-oxadiazol-3-yl}-N-methylpyridin-2-amine | 2090 |
| 3-{5-[2-(3,4-dimethylphenyl)-1-(3-methylphenyl)ethyl]-1,2,4-oxadiazol-3-yl}-N-methylpyridin-2-amine | 50.2 |
| 3-(5-{2-(3,4-dimethylphenyl)-1-[3-(trifluoromethyl)phenyl]ethyl}-1,2,4-oxadiazol-3-yl)-N-methylpyridin-2-amine | 167 |
| 3-{5-[1-(4-chlorophenyl)-2-(3,4-dichlorophenyl)ethyl]-1,2,4-oxadiazol-3-yl}-N-methylpyridin-2-amine | 2020 |
| 3-{5-[2-(3,4-dimethylphenyl)-1-(3-nitrophenyl)ethyl]-1,2,4-oxadiazol-3-yl}-N-methylpyridin-2-amine | 86.4 |
| 3-{5-[2-(3,4-dimethylphenyl)-1-phenylethyl]-1,2,4-oxadiazol-3-yl}-N-methylpyridin-2-amine | 912 |
| 3-{5-[2-(3,4-dimethylphenyl)-1-(3,5-dimethylphenyl)ethyl]-1,2,4-oxadiazol-3-yl}-N-methylpyridin-2-amine | 161 |
| 3-{5-[2-(3,4-dimethylphenyl)-1-(3-thienyl)ethyl]-1,2,4-oxadiazol-3-yl}-N-methylpyridin-2-amine | 296 |
| 3-[5-(1,2-diphenylethyl)-1,2,4-oxadiazol-3-yl]-N-methylpyridin-2-amine | 1240 |
| 3-{5-[1-(6-chloropyridin-3-yl)-2-(3,5-dimethylphenyl)ethyl]-1,2,4-oxadiazol-3-yl}-N-methylpyridin-2-amine | 2760 |

TABLE 2-continued

| IUPAC name | S1P1 EC$_{50}$ (nM) |
|---|---|
| 3-{5-[2-(3,4-dimethylphenyl)-1-(3-ethylphenyl)ethyl]-1,2,4-oxadiazol-3-yl}-N-methylpyridin-2-amine | 61.8 |
| 3-{5-[2-(3,4-dimethylphenyl)-1-(2-thienyl)ethyl]-1,2,4-oxadiazol-3-yl}-N-methylpyridin-2-amine | 524 |
| 3-{5-[1-(3-chlorophenyl)-2-cyclohexylethyl]-1,2,4-oxadiazol-3-yl}-N-methylpyridin-2-amine | 348 |
| 3-{5-[1-(3-chlorophenyl)-2-(3-methylphenyl)ethyl]-1,2,4-oxadiazol-3-yl}-N-methylpyridin-2-amine | 125 |
| N-methyl-3-{5-[2-(4-methylphenyl)-1-(3-thienyl)ethyl]-1,2,4-oxadiazol-3-yl}pyridin-2-amine | 533 |
| 3-{5-[1-(6-chloropyridin-3-yl)-2-(3,4-dimethylphenyl)ethyl]-1,2,4-oxadiazol-3-yl}-N-methylpyridin-2-amine | 274 |
| 3-{5-[1-(3-chlorophenyl)-2-phenylethyl]-1,2,4-oxadiazol-3-yl}-N-methylpyridin-2-amine | 112 |
| 3-{5-[1-(4-chlorophenyl)-2-(3,4-dimethylphenyl)ethyl]-1,2,4-oxadiazol-3-yl}-N-methylpyridin-2-amine | 470 |
| 3-{5-[1-(3-chlorophenyl)-2-cyclopentylethyl]-1,2,4-oxadiazol-3-yl}-N-methylpyridin-2-amine | 1860 |
| 3-(5-{2-(3,4-dimethylphenyl)-1-[4-(trifluoromethyl)phenyl]ethyl}-1,2,4-oxadiazol-3-yl)-N-methylpyridin-2-amine | 2260 |
| 3-{5-[1-(3-bromophenyl)-2-(3,4-dimethylphenyl)ethyl]-1,2,4-oxadiazol-3-yl}-N-methylpyridin-2-amine | 50.6 |
| 3-{5-[1-(3-chlorophenyl)-2-(3,4-dimethylphenyl)ethyl]-1,2,4-oxadiazol-3-yl}-N-methylpyridin-2-amine | 66.4 |
| 3-{5-[1-(3-chlorophenyl)-2-(4-methylphenyl)ethyl]-1,2,4-oxadiazol-3-yl}-N-methylpyridin-2-amine | 78.3 |
| 3-{5-[2-(3,4-dimethylphenyl)-1-(3-fluorophenyl)ethyl]-1,2,4-oxadiazol-3-yl}-N-methylpyridin-2-amine | 35.7 |
| 3-{5-[2-(3,4-dimethylphenyl)-1-(3-methoxyphenyl)ethyl]-1,2,4-oxadiazol-3-yl}-N-methylpyridin-2-amine | 77.6 |
| 3-{5-[1-(4-chlorophenyl)-2-phenylethyl]-1,2,4-oxadiazol-3-yl}-N-methylpyridin-2-amine | 2400 |
| N-methyl-3-{5-[2-(4-methylphenyl)-1-(2-thienyl)ethyl]-1,2,4-oxadiazol-3-yl}pyridin-2-amine | 928 |
| 3-{5-[1-(5-chloropyridin-3-yl)-2-(3,4-dimethylphenyl)ethyl]-1,2,4-oxadiazol-3-yl}-N-methylpyridin-2-amine | 14.5 |
| 3-{5-[1-(3,5-difluorophenyl)-2-(3,4-dimethylphenyl)ethyl]-1,2,4-oxadiazol-3-yl}-N-methylpyridin-2-amine | 12 |

What is claimed is:

1. A method of treating an immunosuppressant disorder associated with the sphingosine-1-phosphate receptor modulation, wherein the immunosuppressant disorder is selected from: psoriasis and multiple sclerosis, in a mammal in need thereof, which comprises administering to a mammal in need thereof, a pharmaceutical composition comprising a therapeutically effective amount of at least one compound represented by Formula I or a pharmaceutically acceptable salt thereof:

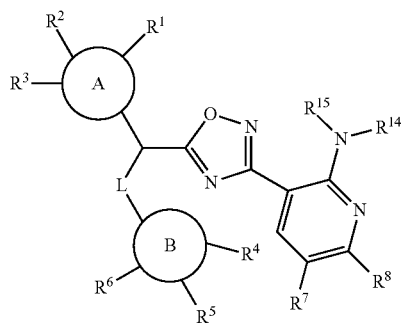

Formula I wherein:
A is $C_6$ aryl or a 5- or 6-membered ring heterocycle;
B is $C_6$ aryl or $C_{3-8}$ cycloalkyl;
$R^1$ is H, halogen, $-OC_{1-8}$ alkyl, $C_{1-8}$ alkyl, CN, C(O)$R^{11}$, NO$_2$, NR$^{12}$R$^{13}$ or hydroxyl;
$R^2$ is H, halogen, $-OC_{1-8}$ alkyl, $C_{1-8}$ alkyl, CN, C(O)$R^{11}$, NO$_2$, NR$^{12}$R$^{13}$ or hydroxyl;
$R^3$ is H, halogen, $-OC_{1-8}$ alkyl, $C_{1-8}$ alkyl, CN, C(O)$R^{11}$, NO$_2$, NR$^{12}$R$^{13}$ or hydroxyl;
$R^4$ is H, halogen, $-OC_{1-6}$ alkyl, $C_{1-8}$ alkyl, CN, C(O)$R^{11}$, NR$^{12}$R$^{13}$ or hydroxyl;
$R^5$ is H, halogen, $-OC_{1-8}$ alkyl, $C_{1-8}$ alkyl, CN, C(O)$R^{11}$, NR$^{12}$R$^{13}$ or hydroxyl;
$R^6$ is H, halogen, $-OC_{1-8}$ alkyl, $C_{1-8}$ alkyl, CN, C(O)$R^{11}$, NR$^{12}$R$^{13}$ or hydroxyl;
$R^7$ is H, halogen, $-OC_{1-8}$ alkyl, $C_{1-8}$ alkyl, CN, C(O)$R^{11}$, NR$^{12}$R$^{13}$ or hydroxyl;
$R^8$ is H, halogen, $-OC_{1-8}$ alkyl, $C_{1-8}$ alkyl, CN, C(O)$R^{11}$, NR$^{12}$R$^{13}$ or hydroxyl;
L is CH$_2$;
$R^{11}$ is H or $C_{1-6}$ alkyl;
$R^{12}$ is H or $C_{1-6}$ alkyl;
$R^{13}$ is H or $C_{1-6}$ alkyl;
$R^{14}$ is H, $C_{1-6}$ alkyl or $C_{3-6}$ cycloalkyl; and
$R^{15}$ is H, $C_{1-6}$ alkyl or $C_{3-6}$ cycloalkyl.

2. The method according to claim 1, wherein said compound is represented by Formula I wherein:

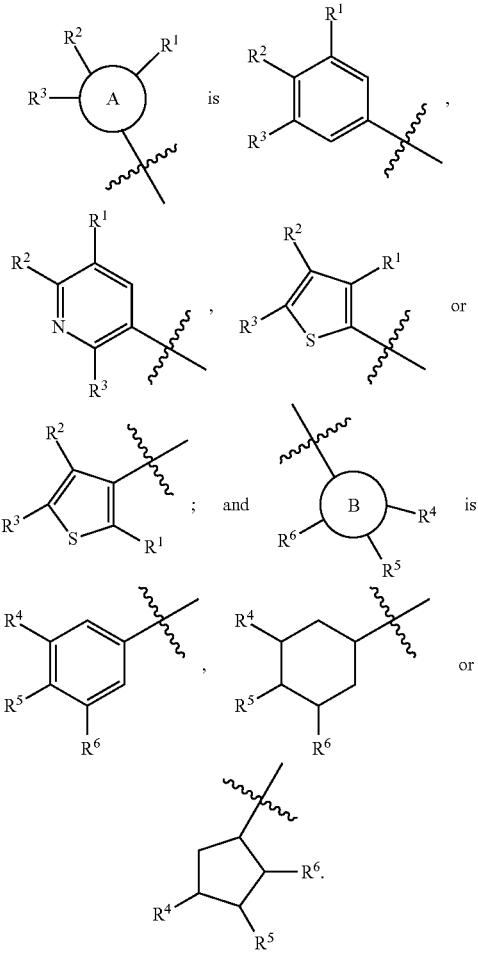

3. The method according to claim 1, wherein said compound is represented by Formula I wherein:

R¹ is H, halogen, —OC$_{1-6}$ alkyl, C$_{1-6}$ alkyl or NO$_2$;
R² is H, halogen, —OC$_{1-6}$ alkyl, C$_{1-6}$ alkyl or NO$_2$;
R³ is H, halogen, —OC$_{1-6}$ alkyl, C$_{1-6}$ alkyl or NO$_2$;
R⁴ is H, halogen or C$_{1-6}$ alkyl,
R⁵ is H, halogen or C$_{1-6}$ alkyl;
R⁶ is H, halogen or —C$_{1-6}$ alkyl;
L is CH$_2$;
R⁷ is H, halogen or C$_{1-6}$ alkyl; and
R⁸ is H, halogen or —C$_{1-6}$ alkyl;
R¹⁴ is H, C$_{1-6}$ alkyl or C$_{3-6}$ cycloalkyl; and
R¹⁵ is H, C$_{1-6}$ alkyl or C$_{3-6}$ cycloalkyl.

4. The method according to claim 1, wherein said compound is represented by Formula I wherein:

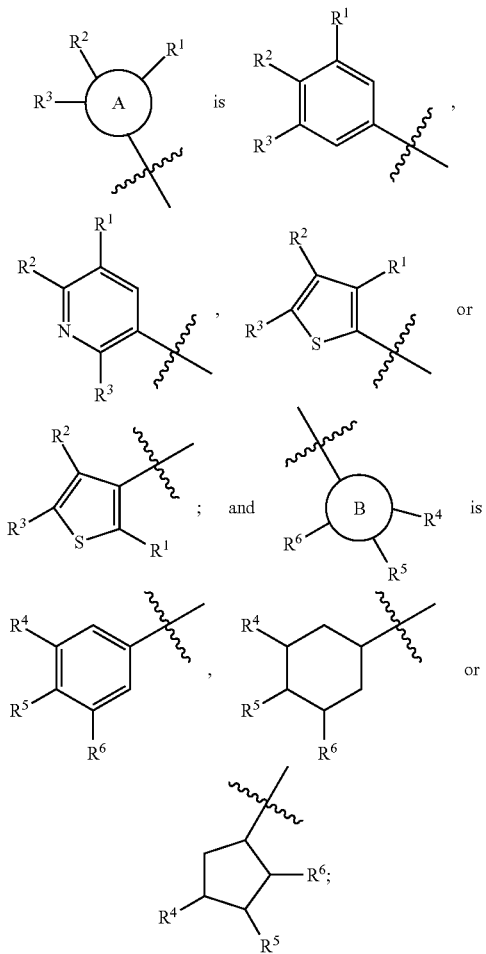

R¹ is H, halogen, —OC$_{1-6}$ alkyl, C$_{1-6}$ alkyl or NO$_2$;
R² is H, halogen, —OC$_{1-6}$ alkyl, C$_{1-6}$ alkyl or NO$_2$;
R³ is H, halogen, —OC$_{1-6}$ alkyl, C$_{1-6}$ alkyl or NO$_2$;
R⁴ is H, halogen or C$_{1-6}$ alkyl,
R⁵ is H, halogen or C$_{1-6}$ alkyl;
R⁶ is H, halogen or —C$_{1-6}$ alkyl;
L is CH$_2$;
R⁷ is H, halogen or C$_{1-6}$ alkyl; and
R⁸ is H, halogen or —C$_{1-6}$ alkyl;
R¹⁴ is H, C$_{1-6}$ alkyl or C$_{3-6}$ cycloalkyl; and
R¹⁵ is H, C$_{1-6}$ alkyl or C$_{3-6}$ cycloalkyl.

5. The method according to claim 1, wherein said compound is represented by Formula I wherein:
R¹ is H, chloro, bromo, fluoro, methyl, ethyl, methoxy or —NO$_2$;
R² is H, chloro, trifluoromethyl, methyl or methoxy;
R³ is H, fluoro or methyl;
R⁴ is H or methyl;
R⁵ is H, methyl, chloro or iso-butyl;
R⁶ is H, methyl or chloro;
R⁷ is H; and
R⁸ is H.

6. The method according to claim 1, wherein said compound is represented by Formula I wherein:
3-{5-[2-(3,4-dimethylphenyl)-1-(3-chlorophenyl)ethyl]-1,2,4-oxadiazol-3-yl}-N-methylpyridin-2-amine;
3-{5-[2-(3,4-dimethylphenyl)-1-(3-bromophenyl)ethyl]-1,2,4-oxadiazol-3-yl}-N-methylpyridin-2-amine;
3-{5-[2-(3,4-dimethylphenyl)-1-(3-fluorophenyl)ethyl]-1,2,4-oxadiazol-3-yl}-N-methylpyridin-2-amine;
3-{5-[2-(3,4-dimethylphenyl)-1-(3-methylphenyl)ethyl]-1,2,4-oxadiazol-3-yl}-N-methylpyridin-2-amine;
3-{5-[2-(3,4-dimethylphenyl)-1-(3-nitrophenyl)ethyl]-1,2,4-oxadiazol-3-yl}-N-methylpyridin-2-amine;
3-{5-[2-(3,4-dimethylphenyl)-1-(3-methoxyphenyl)ethyl]-1,2,4-oxadiazol-3-yl}-N-methylpyridin-2-amine;
3-{5-[2-(3,4-dimethylphenyl)-1-(3-ethyl phenyl)ethyl]-1,2,4-oxadiazol-3-yl}-N-methylpyridin-2-amine;
3-{5-[2-(3,4-dimethylphenyl)-1-phenylethyl]-1,2,4-oxadiazol-3-yl}-N-methylpyridin-2-amine;
3-{5-[2-(3,4-dimethylphenyl)-1-(4-chlorophenyl)ethyl]-1,2,4-oxadiazol-3-yl}-N-methylpyridin-2-amine;
3-{5-[2-(3,4-dimethylphenyl)-1-(4-methoxyphenyl)ethyl]-1,2,4-oxadiazol-3-yl}-N-methylpyridin-2-amine;
3-(5-{2-(3,4-dimethylphenyl)-1-[4-(trifluoromethyl)phenyl]ethyl}-1,2,4-oxadiazol-3-yl)-N-methylpyridin-2-amine;
3-{5-[1-(3-chlorophenyl)-2-phenylethyl]-1,2,4-oxadiazol-3-yl}-N-methylpyridin-2-amine;
3-{5-[1-(4-chlorophenyl)-2-phenylethyl]-1,2,4-oxadiazol-3-yl}-N-methylpyridin-2-amine;
3-{5-[1-(4-chlorophenyl)-2-(3,4-dichlorophenyl)ethyl]-1,2,4-oxadiazol-3-yl}-N-methylpyridin-2-amine;
3-{5-[1-(3-chlorophenyl)-2-(3-methylphenyl)ethyl]-1,2,4-oxadiazol-3-yl}-N-methylpyridin-2-amine;
3-{5-[1-(3-chlorophenyl)-2-(4-methylphenyl)ethyl]-1,2,4-oxadiazol-3-yl}-N-methylpyridin-2-amine;
3-{5-[1-(3-chlorophenyl)-2-(4-isobutylphenyl)ethyl]-1,2,4-oxadiazol-3-yl}-N-methylpyridin-2-amine;
3-{5-[1-(5-chloropyridin-3-yl)-2-(3,4-dimethylphenyl)ethyl]-1,2,4-oxadiazol-3-yl}-N-methylpyridin-2-amine;
3-{5-[1-(6-chloropyridin-3-yl)-2-(3,4-dimethylphenyl)ethyl]-1,2,4-oxadiazol-3-yl}-N-methylpyridin-2-amine;
3-{5-[1-(6-chloropyridin-3-yl)-2-(3,5-dimethylphenyl)ethyl]-1,2,4-oxadiazol-3-yl}-N-methylpyridin-2-amine;
3-{5-[1-(3-chlorophenyl)-2-cyclohexylethyl]-1,2,4-oxadiazol-3-yl}-N-methylpyridin-2-amine;
3-{5-[1-(3-chlorophenyl)-2-cyclopentylethyl]-1,2,4-oxadiazol-3-yl}-N-methylpyridin-2-amine;
N-methyl-3-(5-(1-(thiophen-3-yl)-2-(p-toly)ethyl)-1,2,4-oxadiazol-3-yl)pyridin-2-amine;
3-(5-(2-(3,4-dimethylphenyl)-1-(thiophen-3-yl)ethyl)-1,2,4-oxadiazol-3-yl)-N-methylpyridin-2-amine;
3-(5-(1-(3,5-difluorophenyl)-2-(3,4-dimethylphenyl)ethyl]-1,2,4-oxadiazol-3-yl)-N-methylpyridin-2-amine;

3-(5-(1,2-diphenylethyl)-1,2,4-oxadiazol-3-yl)-N-methylpyridin-2-amine 3-(5-(2-(3,4-dimethylphenyl)-1-(3,5-dimethylphenyl)ethyl)-1,2,4-oxadiazol-3-yl)-N-methylpyridin-2-amine;

N-methyl-3-(5-(1-(thiophen-2-yl)-2-(p-tolyl)ethyl)-1,2,4-oxadiazol-3-yl)pyridin-2-amine;

3-(5-(2-(3,4-dimethylphenyl)-1-(thiophen-2-yl)ethyl)-1,2,4-oxadiazol-3-yl)-N-methylpyridin-2-amine;

3-{5-[1-(3,5-difluorophenyl)-2-(3,4-dimethylphenyl)ethyl]-1,2,4-oxadiazol-3-yl}-N-ethylpyridin-2-amine;

3-{5-[1-(3,5-difluorophenyl)-2-(3,4-dimethylphenyl)ethyl]-1,2,4-oxadiazol-3-yl}-N-propylpyridin-2-amine;

N-cyclobutyl-3-{5-[1-(3,5-difluorophenyl)-2-(3,4-dimethylphenyl)ethyl]-1,2,4-oxadiazol-3-yl}pyridin-2-amine;

3-{5-[1-(3,5-difluorophenyl)-2-(3,4-dimethylphenyl)ethyl]-1,2,4-oxadiazol-3-yl}-N,N-dimethylpyridin-2-amine.

7. The method according to claim 1, wherein the pharmaceutical composition further comprises pharmaceutically acceptable adjuvants, diluents or carriers.

8. The method according to claim 1, wherein the mammal is a human.

* * * * *

UNITED STATES PATENT AND TRADEMARK OFFICE
CERTIFICATE OF CORRECTION

PATENT NO.         : 8,697,733 B2
APPLICATION NO.    : 13/923196
DATED              : April 15, 2014
INVENTOR(S)        : Wenkui K. Fang et al.

It is certified that error appears in the above-identified patent and that said Letters Patent is hereby corrected as shown below:

On the title page, item (56), References Cited under "Other Publications", in column 2, line 1, delete "Nomencalture" and insert -- Nomenclature --, therefor.

On the title page, item (56), References Cited under "Other Publications", in column 2, line 8, delete "Pocker" and insert -- Pocket --, therefor.

On the title page, item (56), References Cited under "Other Publications", in column 2, line 9, delete "Sphingosine 1-Phosphate" and insert -- Sphingosine-1-Phosphate --, therefor.

In the Specification

Column 1, line 29, delete "Sphingosine-1 phosphate" and insert -- Sphingosine-1-phosphate --, therefor.

Column 2, line 34, delete "—OC1-6" and insert -- —OC1-8 --, therefor.

Column 5, line 37, delete "alkyl." and insert -- alkyl; --, therefor.

Column 6, line 22, delete "alkyl," and insert -- alkyl; --, therefor.

Column 6, line 29, delete "$CH_2$." and insert -- $CH_2$; --, therefor.

Column 8, line 21, delete ""—O)P(O)(OH)$_2$"." and insert -- "—(O)P(O)(OH)$_2$". --, therefor.

Column 8, line 42, delete "(3,4-dimethyl phenyl)" and insert -- (3,4-dimethylphenyl) --, therefor.

Column 9, line 17, delete "amine" and insert -- amine; --, therefor.

Column 9, line 55, delete "Stahal & Camille" and insert -- Stahl & Camille --, therefor.

Column 9, line 56, delete "Chemica" and insert -- Chimica --, therefor.

Column 10, line 34, delete "immnuosuppression:" and insert -- immunosuppression: --, therefor.

Column 10, line 37, delete "antoimmune" and insert -- autoimmune --, therefor.

Column 10, line 39, delete "dermititis," and insert -- dermatitis, --, therefor.

Signed and Sealed this
Seventh Day of October, 2014

Michelle K. Lee
*Deputy Director of the United States Patent and Trademark Office*

CERTIFICATE OF CORRECTION (continued)

Column 11, line 30, delete "immnuosuppression:" and insert -- immunosuppression: --, therefor.

Column 11, line 33, delete "antoimmune" and insert -- autoimmune --, therefor.

Column 11, line 35, delete "dermititis," and insert -- dermatitis, --, therefor.

Column 14, line 9, delete "CDl" and. insert -- CDI --, therefor.

Column 14, line 10, delete "EDCl" and insert -- EDCI --, therefor.

Column 14, line 18, delete "CDCl3" and insert -- $CDCl_3$ --, therefor.

Column 14, line 24, delete "ethoxyde" and insert -- ethoxide --, therefor.

Column 15, line 47, delete "hyrdrogen" and insert -- hydrogen --, therefor.

Column 15, line 65, delete "diasteroisomeric" and insert -- diastereoisomeric --, therefor.

Column 33, line 11, delete "methylphenyl)-ethyl]-" and insert -- methylphenyl)ethyl]- --, therefor.

Column 37, lines 48-49, delete "dithitothreitol" and insert -- dithiothreitol --, therefor.

Column 37, line 54, delete "5'-adenylylimmidodiphosphate" and insert -- 5'-adenylylimidodiphosphate --, therefor.

Column 37, line 60, delete "NaCI-100)." and insert -- NaCl-100). --, therefor.

In the Claims

Column 40, line 7, claim 1, delete "—$OC_{1-6}$ alkyl," and insert -- —$OC_{1-8}$ alkyl, --, therefor.

Column 41, line 4, claim 3, delete "alkyl," and insert -- alkyl; --, therefor.

Column 41, line 56, claim 4, delete "alkyl," and insert -- alkyl; --, therefor.

Column 42, line 1, claim 5, delete "methoxy," and insert -- methoxy; --, therefor.

Column 42, line 24, claim 6, delete "(3-ethyl phenyl)ethyl]-1," and insert -- 3-ethylphenyl)ethyl]-1, --, therefor.

Column 43, line 2, claim 6, delete "amine" and insert -- amine; --, therefor.